(12) United States Patent
Jeon et al.

(10) Patent No.: US 10,907,222 B2
(45) Date of Patent: Feb. 2, 2021

(54) PRIMERS FOR DETECTING INFLUENZA BY USING LAMP, AND USE THEREOF

(71) Applicant: MMONITOR INC., Daegu (KR)

(72) Inventors: Hyo Sung Jeon, Daegu (KR); Su Jeong Shin, Daegu (KR); Ji Jung Kim, Daegu (KR)

(73) Assignee: MMONITOR INC., Daegu (KR)

( * ) Notice: Subject to any disclaimer, the term of this patent is extended or adjusted under 35 U.S.C. 154(b) by 78 days.

(21) Appl. No.: 15/744,709

(22) PCT Filed: Aug. 17, 2016

(86) PCT No.: PCT/KR2016/009016
§ 371 (c)(1),
(2) Date: Jan. 12, 2018

(87) PCT Pub. No.: WO2017/034207
PCT Pub. Date: Mar. 2, 2017

(65) Prior Publication Data
US 2019/0002994 A1   Jan. 3, 2019

(30) Foreign Application Priority Data

Aug. 21, 2015  (KR) ..................... 10-2015-0117834
Dec. 24, 2015  (KR) ..................... 10-2015-0185750

(51) Int. Cl.
*C12Q 1/70* (2006.01)
*C12Q 1/68* (2018.01)
*C12Q 1/6806* (2018.01)
*C12Q 1/686* (2018.01)

(52) U.S. Cl.
CPC ................ *C12Q 1/70* (2013.01); *C12Q 1/68* (2013.01); *C12Q 1/6806* (2013.01); *C12Q 1/686* (2013.01); *C12Q 2600/112* (2013.01); *C12Q 2600/16* (2013.01)

(58) Field of Classification Search
CPC ........ C12Q 1/68; C12Q 1/6806; C12Q 1/686; C12Q 1/70; C12Q 1/701; C12Q 2600/112; C12Q 2600/16
See application file for complete search history.

(56) References Cited

U.S. PATENT DOCUMENTS

| 8,389,221 B2 | 3/2013 | Minekawa et al. |
| 2008/0305472 A1 | 12/2008 | Seki et al. |
| 2015/0184255 A1 | 7/2015 | Cai et al. |

FOREIGN PATENT DOCUMENTS

| CN | 101608242 A | 12/2009 |
| CN | 103497947 A | 1/2014 |
| WO | 2006-043349 A1 | 4/2006 |
| WO | 2006043349 A1 | 4/2006 |

OTHER PUBLICATIONS

Kubo et al., J. Clinical Microbiology, 48(3): 729-735, (Year: 2010).*
Mahoiny et al., "Multiplex loop-mediated isothermal amplification (M-LAMP) assay for the detection of influenza A/H1, A/H3 and influenza B can provide a specimen-to-result diagnosis in 40 min with single genome copy sensitivity", Journal of Clinical Virology, 58, 127-131, (Jun. 4, 2013).
Gu et al., "Rapid and specific detection on H3 swine influenza virus using reverse transcription loop-mediated isothermal amplification method", Journal of Applied Mircorbiology, 108, 1145-1154, (Apr. 2010).
Jung et al., "Combination of multiplex reverse-transcription loop-mediated isothermal amplification with an immunochromatographic strip for subtyping influenza A virus", Analytica Chimica Acta, 853, 541-547, Oct. 16, 2014.
Webster et al., "Evolution and Ecology of Influenza A Viruses", Mircobiology Reviews, Mar. 1992.
Webby, R. J., and R. G. Webster, "Are we ready for pandemic influenza?", Science 302:1519-1522, Nov. 28, 2003.
Nicholson, K. G., Wood, J. M., & Zambon, M., "Influenza." Lancet, 362 (9397), 1733-1745), Nov. 22, 2003.
Fouchier et al., "Characterization of a Novel Influenza A Virus Hemagglutinin Subtype (H16) Obtained from Black-Headed Gulls", Journal of Virology, Mar. 2005.
Mahony et al., "Multiplex loop-mediated isothermal amplification (M-LAMP) assay for the detection of influenza A/H1, A/H3 and influenza B can provide a specimen-to-result diagnosis in 40 min with single genome copy sensitivity" Journal of Clinical Virology, vol. 58, pp. 127-131, Jul. 1, 2013.
Gu et al., "Rapid and specific detection of H3 swine influenza virus using reverse transcription loop-mediated isothermal amplification method" Journal of Applied Microbiology, vol. 108, pp. 1145-1154, Apr. 2010.
Jung et al., "Combination of multiplex reverse-transcription loop-mediated isothermal amplification with an immunochromatographic strip for subtyping influenza A virus" Analytica Chimica Acta, vol. 853, pp. 541-547, Jan. 1, 2015.

\* cited by examiner

*Primary Examiner* — Cynthia B Wilder
(74) *Attorney, Agent, or Firm* — Maschoff Brennan

(57) ABSTRACT

Disclosed are: a primer set enabling the specific detection, by an isothermal amplification method, of an influenza A virus, an influenza A subtype H3 virus, an influenza A subtype pdm H1N1 virus, and an influenza B virus; a composition or a kit comprising the same; and a method for detecting influenza viruses by using the same. The primers and the method, according to the present application, can detect, in a rapid manner and with high sensitivity and specificity, whether influenza virus infection occurs, and enable detection without separate treatments after the completion of the amplification, thereby improving convenience.

20 Claims, 11 Drawing Sheets

Specification includes a Sequence Listing.

1

PRIMERS FOR DETECTING INFLUENZA BY USING LAMP, AND USE THEREOF

TECHNICAL FIELD

The present invention relates to primers for detecting influenza using a loop-mediated isothermal amplification (LAMP) technique and use thereof.

The sequence listing disclosed herein is included in a text file having the name "M2523.10139US01_Sequence_Listing," created on Jun. 13, 2016, having a size of 15000 bytes. The foregoing text file is incorporated herein by reference.

BACKGROUND ART

Influenza, a pathogenic virus which is considered to be medically important, has caused serious damage to humans around the world, thereby leading to tremendous economic losses. Influenza A and B viruses belong to Orthomyxoviridae, are RNA viruses whose genomes are made of negative-sense single-stranded RNA having eight segments (Webster et al. 1992; Fouchier et al. 2005), and include 15 hemagglutinin subtypes and 9 neuraminidase subtypes.

Of these, only three hemagglutinin subtypes (H1 to H3) and two neuraminidase subtypes (N1 and N2) have been safely established in humans (Webby, R. J., and R. G. Webster. 2003. Are we ready for pandemic influenza? Science 302:1519-1522; Nicholson, K. G., Wood, J. M., & Zambon, M. (2003). Influenza. Lancet, 362 (9397), 1733-1745).

Since influenza viruses are highly infectious and spread quickly to the areas located nearby from an area affected by influenza, early identification and detection of influenza are critical in establishing preventive measures against influenza.

Detection methods using various molecular biological techniques have been developed to detect influenza viruses.

US Patent Publication No. 2015-0184255 relates to a system and method for detecting the nucleic acids of influenza viruses and discloses techniques for detecting the nucleic acids of influenza viruses present in clinical samples by using HDA isothermal amplification and lateral flow analysis.

In addition, U.S. Pat. No. 8,389,221 discloses a method of detecting an H5 or H7 avian influenza virus.

However, there is a need for a method of detecting various kinds of influenza viruses on the basis of new techniques enabling effective detection with higher sensitivity and specificity.

DISCLOSURE

Technical Problem

The present invention is directed to providing a method for rapidly and easily detecting influenza virus infection with high sensitivity and specificity.

Technical Solution

The present invention is to provide a primer set capable of even distinguishing the subtypes of influenza a primer set capable of detecting all subtypes of influenza A, or a primer set capable of distinguishing influenza B from other types of influenza, and use thereof for detecting influenza.

According to one aspect of the present invention, to detect influenza viruses, provided is a primer set for LAMP analysis for detecting influenza viruses, being selected from the group consisting of: an influenza A subtype H3-specific primer set including four primers respectively represented by sequence (SEQ) numbers SEQ ID NO: 1 to SEQ ID NO: 4, four primers respectively represented by SEQ ID NO: 7 to SEQ ID NO: 10, or four primers respectively represented by SEQ ID NO: 13 to SEQ ID NO: 16; an influenza A subtype pdm H1N1-specific primer set including four primers respectively represented by SEQ ID NO: 19 to SEQ ID NO: 22, four primers respectively represented by SEQ ID NO: 21, SEQ ID NO: 22, SEQ ID NO: 25, and SEQ ID NO: 26, or four primers respectively represented by SEQ ID NO: 29 to SEQ ID NO: 32; a primer set specific for all subtypes of influenza A including four primers respectively represented by SEQ ID NO: 35 to SEQ ID NO: 38, four primers respectively represented by SEQ ID NO: 41 to SEQ ID NO: 44, or four primers respectively represented by SEQ ID NO: 47 to SEQ ID NO: 50; and an influenza B-specific primer set including four primers respectively represented by SEQ ID NO: 52 to SEQ ID NO: 55, four primers respectively represented by SEQ ID NO: 58 to SEQ ID NO: 61, four primers respectively represented by SEQ ID NO: 64 to SEQ ID NO: 67, or four primers respectively represented by SEQ ID NO: 70 to SEQ ID NO: 73.

The primer set according to the present invention may quickly and exactly detect influenza viruses having different genotypes with high sensitivity.

In one embodiment, the primer sets according to the present invention may be used in RT-LAMP using RNA as a template, and each of the above-mentioned primer set may further include primers sets additionally including two primers. In one embodiment, the respective primer sets specific for influenza A subtype H3 of the present invention may further include primers represented by SEQ ID NO: 5 and SEQ ID NO: 6, SEQ ID NO: 11 and SEQ ID NO: 12, or SEQ ID NO: 17 and SEQ ID NO: 18. Specifically, the primer set including primers represented by SEQ ID NO: 1 to SEQ ID NO: 4 may further include primers represented by SEQ ID NO: 5 and SEQ ID NO: 6; the primer set including primers represented by SEQ ID NO: 7 to SEQ ID NO: 10 may further include primers represented by SEQ ID NO: 11 and SEQ ID NO: 12; and the primer set including primers represented by SEQ ID NO: 13 to SEQ ID NO: 16 may further include primers represented by SEQ ID NO: 17 and SEQ ID NO: 18. The primer set specific for influenza A subtype pdm H1N1 may further include primers represented by SEQ ID NO: 23 and SEQ ID NO: 24, SEQ ID NO: 27 and SEQ ID NO: 28, or SEQ ID NO: 33 and SEQ ID NO: 34. Specifically, the primer set including primers represented by SEQ ID NO: 19 to SEQ ID NO: 22 may further include primers represented by SEQ ID NO: 23 and SEQ ID NO: 24; the primer set including primers represented by SEQ ID NO: 21, SEQ ID NO: 22, SEQ ID NO: 25, and SEQ ID NO: 26 may further include primers represented by SEQ ID NO: 27 and SEQ ID NO: 28; and the primer set including primers represented by SEQ ID NO: 29 to SEQ ID NO: 32 may further include primers represented by SEQ ID NO: 33 and SEQ ID NO: 34. The primer set specific for all subtypes of influenza A may further include primers represented by SEQ ID NO: 39 to SEQ ID NO: 40, SEQ ID NO: 45 to SEQ ID NO: 46, or SEQ ID NO: 51 to SEQ ID NO: 46. Specifically, the primer set including primers represented by SEQ ID NO: 35 to SEQ ID NO: 38 may further include primers represented by SEQ ID NO: 39 and SEQ ID NO: 40; the primer set including primers represented by SEQ ID NO: 41 to SEQ ID NO: 44 may further include primers represented by SEQ ID NO: 45 and SEQ ID NO: 46; and the primer set including primers represented by SEQ ID NO: 47 to SEQ ID NO: 50 may further include primers represented by SEQ ID NO: 51 and SEQ ID NO: 46. The primer set specific for influenza B may further include primers represented by SEQ ID NO: 56 and SEQ ID NO: 57, SEQ ID NO: 62 and SEQ ID NO: 63, SEQ ID NO: 68 and SEQ ID NO: 69, or SEQ ID NO: 74 and SEQ ID NO: 75. Specifically, the primer set including primers represented by SEQ ID NO: 52 to SEQ ID NO: 55 may further include primers represented by SEQ ID NO: 56 and SEQ ID NO: 57; the primer set including primers represented by SEQ ID NO: 58 to SEQ ID NO: 61 may further include primers represented by SEQ ID NO: 62 and SEQ ID NO: 63; the primer set including primers represented by SEQ ID NO: 64 to SEQ ID NO: 67 may further include primers represented by SEQ ID NO: 68 and SEQ ID NO: 69; and the primer set including primers represented by SEQ ID NO: 70 to SEQ ID NO: 73 may further include primers represented by SEQ ID NO: 74 and SEQ ID NO: 75.

In accordance with another aspect of the present invention, provided is a primer set for a LAMP analysis to detect influenza viruses, the primer set being selected from the group consisting of: an influenza A subtype H3-specific primer set including primers having base sequences represented by SEQ ID NO: 1 to SEQ ID NO: 4, SEQ ID NO: 7 to SEQ ID NO: 10, or SEQ ID NO: 13 to SEQ ID NO: 16; an influenza A subtype pdm H1N1-specific primer set including primers having base sequences represented by SEQ ID NO: 19 to SEQ ID NO: 22, SEQ ID NO: 21, SEQ ID NO: 22, SEQ ID NO: 25, and SEQ ID NO: 26, or SEQ ID NO: 29 to SEQ ID NO: 32; a primer set specific for all subtypes of influenza A including primers having base sequences represented by SEQ ID NO: 35 to SEQ ID NO: 38, SEQ ID NO: 41 to SEQ ID NO: 44, or SEQ ID NO: 47 to SEQ ID NO: 50; and an influenza B-specific primer set including primers having base sequences represented by SEQ ID NO: 52 to SEQ ID NO: 55, SEQ ID NO: 58 to SEQ ID NO: 61, SEQ ID NO: 64 to SEQ ID NO: 67, or SEQ ID NO: 70 to SEQ ID NO: 73.

The primer set according to the present invention may further include two primers. Specifically, the influenza A subtype H3-specific primer set may further include primers represented by SEQ ID NO: 5 and SEQ ID NO: 6, SEQ ID NO: 11 and SEQ ID NO: 12, or SEQ ID NO: 17 and SEQ ID NO: 18; the influenza A subtype pdm H1N1-specific primer set may further include primers represented by SEQ ID NO: 23 and SEQ ID NO: 24, SEQ ID NO: 27 and SEQ ID NO: 28, or SEQ ID NO: 33 and SEQ ID NO: 34; the primer set specific for all subtypes of influenza A may further include primers represented by SEQ ID NO: 39 and SEQ ID NO: 40, SEQ ID NO: 45 and SEQ ID NO: 46, or SEQ ID NO: 51 and SEQ ID NO: 46; and the influenza B-specific primer set may further include primers represented by SEQ ID NO: 56 and SEQ ID NO: 57, SEQ ID NO: 62 and SEQ ID NO: 63, SEQ ID NO: 68 and SEQ ID NO: 69, or SEQ ID NO: 74 and SEQ ID NO: 75.

The primers according to the present invention may be labeled with one or more detectable labeling substances depending on methods of detecting amplified signals.

In accordance with another aspect of the present invention, provided is a method of detecting influenza viruses in vitro using the primer set disclosed herein, the method including a step of providing samples taken from subjects requiring influenza virus detection; a step of providing any one primer set of the primer sets according to the present invention; a step of performing a LAMP reaction using the samples and the primer set; and a step of analyzing results of the LAMP reaction and comparing LAMP reaction results of the samples with LAMP reaction results of control samples to determine whether the samples are infected with influenza.

In one embodiment, a LAMP reaction according to the present invention may be RT-LAMP.

In the method using the primer set according to the present invention, various samples, in which influenza viruses may be detected, may include whole blood, plasma, serum, lymph, urine, saliva, tears, and nasopharyngeal secretions, without being limited thereto.

In the method according to the present invention, the step of analyzing results of the LAMP reaction may be performed by measuring one or more of the color change and/or the turbidity of the reactants. Such a measurement method may increase the convenience of the present invention.

In accordance with yet another aspect of the present invention, provided is a composition or kit for detecting influenza viruses including the primer set according to the present invention.

Advantageous Effects

As apparent from the fore-going, the present invention advantageously provides a primer set capable of specifically detecting influenza A, influenza A subtype H3, influenza A subtype pdm H1N1, or influenza B using an isothermal amplification method, a composition or kit including the same, and a method of detecting influenza viruses using the same. The primer and the method, according to the present invention, can be used to quickly detect influenza virus infection with high sensitivity and specificity. When the primer and the method are used to perform an amplification reaction for detecting influenza viruses, it is possible to determine whether influenza virus infection occurs without any additional analysis, such as electrophoresis, after the amplification reaction is terminated, thereby increasing convenience.

DESCRIPTION OF DRAWINGS

In FIG. 4B, influenza B was used as a control group.

BEST MODE

Figure 1:
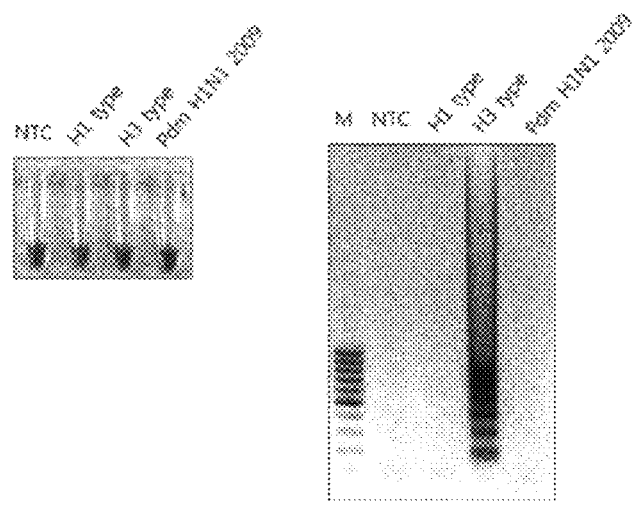
FIG. 1 shows the results of detecting the specificity of an influenza A subtype H3-specific LAMP primer set having primers represented by SEQ ID NO: 7 to SEQ ID NO: 12 via color changes and agarose gel electrophoresis.

The present invention is based on the discovery that influenza may be easily detected with high accuracy and sensitivity at the nucleic acid level using a LAMP technique, and relates to a primer set capable of specifically detecting influenza A, influenza A subtype H3, influenza A subtype pdm H1N1, or influenza B using loop-mediated isothermal amplification (LAMP), and use thereof. As the use of the primer set according to the present invention, the present invention relates to a composition or kit including the primer set, and a method of detecting influenza viruses using the primer set or the composition or kit.

In one embodiment, the present invention relates to a primer set for a LAMP analysis to specifically detect influenza A, influenza A subtype H3, influenza A subtype pdm H1N1, or influenza B.

As used herein, the term "primer" refers to a nucleic acid molecule composed of single-stranded oligonucleotides, and nucleotides may be added and extended by covalent bonds at the 3' terminus of the primer during a reaction of nucleic acid amplification or synthesis using a polymerase. The primer set according to the present invention is used for amplification of nucleic acids, that is, for a LAMP analysis or a RT-LAMP analysis.

As used herein, the term "nucleic acids" refer to RNA or DNA molecules or analogs and derivatives thereof including one or more nucleotides of any form, including single- or double-stranded oligonucleotides or polyoligonucleotides. The nucleic acids of an influenza virus to be detected using the primer set according to the present invention include RNA derived from the influenza virus, for example, all or a part of the genome of the influenza virus, or DNA corresponding thereto.

As used herein, the term "oligonucleotides" and "polynucleotides" are used interchangeably, and either one may include both. Also, the term "primer" may be used interchangeably with "oligonucleotides" and "polynucleotides", and includes nucleic acids (RNA or DNA), aptamers, and the like.

As used herein, the term "detection" includes determining whether influenza viruses are infected, or determining the prognosis of an infected subject, and determining recurrence after infection treatment or therametrics (e.g., monitoring the status of the subject to provide information about the therapeutic efficacy).

As used herein, the term "target" or "target nucleic acids" refers to a nucleic acid sequence to which the primer set of the present invention binds and is specifically amplified by the primer set according to the present invention, and includes RNA or DNA.

The primer according to the present invention specifically binds to target nucleic acids through complementation and is used to amplify the target nucleic acids using a LAMP technique. Loop-mediated isothermal amplification (LAMP) is a method of amplifying target nucleic acids with high sensitivity and specificity under isothermal conditions (Notomi, T. et al. 2000. Loop-Mediated Isothermal Amplification of DNA. Nucleic Acids Res 28, E63). The LAMP method includes a standard method, in which a DNA polymerase having a strand displacement activity and a primer set consisting of at least four primers specific to the several regions of target nucleic acids are included (see Korean Patent No. 612551), a method, in which six primers are used as a primer set (see Nagamine, K. et al. 2002. Accelerated reaction by Loop mediated isothermal amplification using loop primers. Mol Cell Probes 16, 223-9), and a method, in which reverse transcription is used, i.e., RT-LAMP, (see Yoshida, N. et al 2007. Simple differentiation method of mumps Hoshino vaccine strain from wild strains by RT-LAMP. Vaccine 25, 1281-6).

As used herein, the term "complementary" or "complementarity" refers to a condition in which a primer or oligonucleotides can bind sequence-specifically to target nucleic acids through the Watson-Crick base pairing under hybridization, binding or annealing conditions, and includes partial complementarity, substantial complementarity and perfect complementarity. Substantial complementarity means that two strands of nucleic acid sequences are not completely complementary to each other, but are complementary enough to bind to target nucleic acids so as to amplify the effect according to the present invention, that is, amplify the target sequence through the LAMP method.

As used herein, the term "hybridization" refers to a reaction in which two strands of complementary nucleic acid molecules form a sequence-specific complex through hydrogen bonding. Hybridization may constitute a step of binding a primer to target nucleic acids or a template in a LAMP reaction in which the primer according to the present invention is used. The degree of hybridization is affected by various factors, such as the degree of complementarity of any two nucleic acid molecules, melting temperatures (Tm)

thereof, or the stringency of hybridization. The hybridization reaction conditions may also be determined by considering these factors. The stringency of a hybridization reaction is a condition that determines how easily any two nucleic acid molecules to be hybridized can bind to each other, and the stringency may be determined depending on complementarity, reaction temperatures, ionic strength and/or concentrations and types of common substances included in a hybridization reaction solution (see J. Sambrook and D. W. Russell, Molecular Cloning: A Laboratory Manual, Cold Spring Harbor Laboratory Press; 4th Ed., 2012; and F. M. Ausubel, Ed., Short Protocols in Molecular Biology, Wiley; 5th Ed, 2002).

Specific binding or hybridization herein means that a particular nucleic acid molecule or primer binds only to target nucleic acids without substantial binding to nucleic acids other than target nucleic acids. The primers according to the present invention may specifically bind to target influenza nucleic acids according to the present invention or the complementary sequence thereof under high stringency conditions. In the case of template-based DNA synthesis, it may be determined in consideration of the length of a primer sequence, buffer, nucleic acid type, pH, magnesium concentration, and reaction temperature.

The primers according to the present invention are designed to specifically detect influenza A subtype H3, influenza A pdm H1N1 (or influenza A pdm H1N1 2009), influenza B, influenza A (regardless of subtypes), and specifically bind to each of target nucleic acids or complementary sequence thereof. In one embodiment, the primer sets according to the present invention are designed to specifically recognize the regions of the hemagglutinin (HA) gene, the matrix genes, and the neuraminidase (NA) gene and to detect viruses with high sensitivity.

The regions in which the primers according to the present invention are designed are regions with low specificity among subtypes (e.g., influenza A subtypes H1, H3, and H5). Thus, according to the amplification characteristics of LAMP, when a target sequence is selectively amplified based on some difference of primer sequences, nonspecific amplification may occur when a high concentration of sample is added. Therefore, it is very important to prevent such nonspecific amplification, and nonspecific amplification does not occur when the primers according to the present invention are used.

As described above, when a LAMP reaction or RT-LAMP is performed, at least 4 primers are used: forward inner primer (FIP), backward inner primer (BIP), forward outer primer (F3), and backward outer primer (B3). In addition, loop F (LF) and loop B (LB) may be further included for rapid reaction, thus a total of six primers may be used. For the features and functions of F3, B3, FIP, BIP, LF, and LB, the above-mentioned references (Notomi et al., 2000 and Nagamine et al., 2002) may be referred.

Primers that specifically bind to the target nucleic acids or the complementary sequences thereof according to the present invention have a length of at least 10 nucleotides. F3 and B3 have a length of at least 10 nucleotides, FIP and BIP have a length of at least 25 nucleotides, and LF and LB have a length of at least 15 nucleotides. The primers have at least 70% complementarity, preferably 80% complementarity, more preferably 90% complementarity, most preferably 95%, 96%, 97%, 98%, 99%, or 100% complementarity, with a portion corresponding to target nucleic acids.

In one embodiment, the primers according to the present invention include primers represented by SEQ ID NO: 1 to SEQ ID NO: 75 and primers having sequences substantially identical to the sequences of the primers represented by SEQ ID NO: 1 to SEQ ID NO: 75, and bind to target nucleic acids or complementary sequences thereof. The primers having sequences substantially identical to the sequences of the primers represented by SEQ ID NO: 1 to SEQ ID NO: 75 have a complementarity of 70%, preferably a complementarity of 80%, more preferably a complementarity of 90%, most preferably a complementarity of 95%, 96%, 97%, 98%, 99%, or 100%, with the primers represented by SEQ ID NO: 1 to SEQ ID NO: 75. In the case of FIP and BIP, as described below, two sequences that bind to target nucleic acids and the complementary sequence thereof may be linked by a linker that does not bind to the target nucleic acids. In this case, complementarity refers to complementarity with a portion excluding the linker portion.

The LAMP primer according to the present invention specifically binds to the target sequence of influenza A subtype H3, influenza A subtype pdm H1N1, influenza B, or all subtypes of influenza A.

In one embodiment, the LAMP primer set capable of specifically detecting influenza A according to the present invention includes FIP selected from SEQ ID NO: 1, 7, 13, 19, 25, 29, 35, 41, or 47, BIP selected from SEQ ID NO: 2, 8, 14, 20, 26, 30, 36, 42, or 48, F3 selected from SEQ ID NO: 3, 9, 15, 21, 31, 37, 43, or 49, and B3 selected from SEQ ID NO: 4, 10, 16, 22, 32, 38, 44, or 50. In another embodiment, the primer set capable of specifically detecting influenza A includes FIP selected from SEQ ID NO: 1, 7, 13, 19, 25, 29, 35, 41, or 47, BIP selected from SEQ ID NO: 2, 8, 14, 20, 26, 30, 36, 42, or 48, F3 selected from SEQ ID NO: 3, 9, 15, 21, 31, 37, 43, or 49, B3 selected from SEQ ID NO: 4, 10, 16, 22, 32, 38, 44, or 50, LF selected from SEQ ID NO: 5, 11, 17, 23, 27, 33, 39, 45, or 51, and LB selected from SEQ ID NO: 6, 12, 18, 24, 28, 34, 40, or 46.

In one embodiment, the primer set capable of specifically detecting influenza A subtype H3 using a LAMP technique includes primers represented by SEQ ID NO: 1 to SEQ ID NO: 4, primers represented by SEQ ID NO: 7 to SEQ ID NO: 10, primers represented by SEQ ID NO: 13 to SEQ ID NO: 16, or primers having sequences substantially identical to the sequences thereof. In another embodiment, the primer set capable of specifically detecting influenza A subtype H3 using a LAMP technique includes primers represented by SEQ ID NO: 1 to SEQ ID NO: 6, primers represented by SEQ ID NO: 7 to SEQ ID NO: 12, primers represented by SEQ ID NO: 13 to SEQ ID NO: 18, or primers having sequences substantially identical to the sequences thereof.

In one embodiment, the primer set capable of specifically detecting influenza A subtype pdm H1N1 using a LAMP technique includes primers represented by SEQ ID NO: 19 to SEQ ID NO: 22, primers represented by SEQ ID NO: 21, SEQ ID NO: 22, and SEQ ID NO: 25 to SEQ ID NO: 26, primers represented by SEQ ID NO: 29 to SEQ ID NO: 32, or primers having sequences substantially identical to the sequences thereof. In another embodiment, the primer set capable of specifically detecting influenza A subtype pdm H1N1 includes primers represented by SEQ ID NO: 19 to SEQ ID NO: 24, primers represented by SEQ ID NO: 21, SEQ ID NO: 22, and SEQ ID NO: 25 to SEQ ID NO: 28, primers represented by SEQ ID NO: 29 to SEQ ID NO: 34, or primers having sequences substantially identical to the sequences thereof. The primers represented by SEQ ID NO: 19 to SEQ ID NO: 24 and the primers represented by SEQ ID NO: 25 to SEQ ID NO: 28 were synthesized using matrix gene sequences.

In one embodiment, the primer set capable of specifically detecting all subtypes of influenza A using a LAMP technique includes primers represented by SEQ ID NO: 35 to SEQ ID NO: 38, primers represented by SEQ ID NO: 41 to SEQ ID NO: 44, primers represented by SEQ ID NO: 47 to SEQ ID NO: 50, or primers having sequences substantially identical to the sequences thereof. In another embodiment, the primer set capable of specifically detecting all subtypes of influenza A includes primers represented by SEQ ID NO: 35 to SEQ ID NO: 40, primers represented by SEQ ID NO: 41 to SEQ ID NO: 46, primers represented by SEQ ID NO: 46 and SEQ ID NO: 47 to SEQ ID NO: 51, or primers having sequences substantially identical to the sequences thereof. The primers represented by SEQ ID NO: 41 to SEQ ID NO: 46 and the primers represented by SEQ ID NO: 46 and SEQ ID NO: 47 to SEQ ID NO: 51 were designed in a region similar to the matrix genes, and these primers exhibited partial differences (within 5 bp per primer) in nucleotide sequences except for a LB primer.

In one embodiment, the primer set capable of specifically detecting influenza B using a LAMP technique includes primers represented by SEQ ID NO: 52 to SEQ ID NO: 55, primers represented by SEQ ID NO: 58 to SEQ ID NO: 61, primers represented by SEQ ID NO: 64 to SEQ ID NO: 67, primers represented by SEQ ID NO: 70 to SEQ ID NO: 73, or primers having sequences substantially identical to the sequences thereof. In another embodiment, the primer set capable of specifically detecting influenza B includes primers represented by SEQ ID NO: 52 to SEQ ID NO: 57, primers represented by SEQ ID NO: 58 to SEQ ID NO: 63, primers represented by SEQ ID NO: 64 to SEQ ID NO: 69, primers represented by SEQ ID NO: 70 to SEQ ID NO: 75, or primers having sequences substantially identical to the sequences thereof. The primers represented by SEQ ID NO: 52 to SEQ ID NO: 57 and the primers represented by SEQ ID NO: 64 to SEQ ID NO: 69 were designed in a NEP NS1 gene region, and the primers represented by SEQ ID NO: 58 to SEQ ID NO: 63 and the primers represented by SEQ ID NO: 70 to SEQ ID NO: 75 were designed in a HA gene region.

The primer according to the present invention, a composition or kit including the same, and a method using the same may be used for analysis of any biological samples in need of detection of influenza viruses.

In one embodiment, a biological sample is typically a liquid or cell or tissue sample of mammals, including humans. Samples which may be used herein include whole blood, plasma, serum, lymph, urine, saliva, tears, nasopharyngeal secretions, and breast milk, without being limited thereto. In addition, the samples include blood and cell or tissue fractions or derivatives thereof. When cells or tissues are used as a sample, cells themselves or the lysates of cells or tissues may be used.

In one embodiment, samples derived from subjects requiring influenza virus detection include samples obtained from subjects expected to or need to detect influenza viruses.

In another embodiment, biological samples may be in the form of dried liquid or tissue samples.

In addition, these biological samples may be obtained directly from subjects by a conventional method of obtaining samples requiring influenza detection immediately before a test, or may be previously isolated and stored.

In another embodiment, tissues/cells obtained from a subject or in vitro cell cultures in need of influenza detection may be used as a sample, without being limited thereto.

In one embodiment according to the present invention, nasopharyngeal secretions may be directly used as a sample or the nucleic acids extracted therefrom may be used as a sample.

In addition, in another embodiment, the nucleic acids extracted from the above-described liquid or tissue samples may be used as the biological sample. Extraction refers to separation of nucleic acids from a sample containing the nucleic acids, and nucleic acids having various purity may be extracted.

The primer according to the present invention, a composition or kit including the same, and a method using the same are used to analyze any biological sample that may be infected with influenza viruses by a LAMP technique.

In a reaction for a LAMP analysis, the primer set according to the present invention, dNTPs, a buffer solution, magnesium, a DNA polymerase, and a biological sample requiring influenza detection are used. In addition, substances, such as betaine or DMSO, to enhance the reaction may be further included.

An influenza virus is a RNA virus. When RNA is used as a template in a LAMP analysis, a reverse transcriptase may be additionally added to the reactant of the LAMP analysis and RT-LAMP may be performed.

The primer set added to the reaction is as described above, and four or six primers may be included in the primer set.

Magnesium is used in the form of a salt, such as magnesium acetate, magnesium chloride, or magnesium sulfate.

A sodium phosphate buffer, a potassium phosphate buffer, a Tris-HCl buffer, or a Tricine buffer may be used as a buffer solution.

The DNA polymerase that may be used in a reaction is a polymerase derived from a thermophilic microorganism, in particular, a polymerase lacking a 5'→3' exonuclease function. Non-limiting examples of the DNA polymerase include the *Bacillus stearothermophilus* (Bst) DNA polymerase, the *Thermus, thermophilus* (Tth) DNA polymerase, the *Thermus aquaticus* (Taq) DNA polymerase, the *Thermococcus litoralis* DNA polymerase, the *Pyrococcus furiosus* (Pfu) DNA polymerase, and the *Bacillus caldotenax* DNA polymerase.

Non-limiting examples of reverse transcriptases that may be used in a reaction include the moloney murine leukemia virus (MMLV) reverse transcriptase and the avian myeloblastosis virus (AMV) reverse transcriptase.

In addition, nucleotide analogs may be used in place of dNTPs in a reactant. The nucleotide analogs may be modified nucleotides or nucleotides that are not found in nature, and may be polymerized either alone or in conjunction with natural nucleotides during DNA synthesis. Specific examples of nucleotide analogues that may be polymerized through the Watson-Crick base pairing include substituted purines or pyrimidines, deazapurines, methylpurines, methylpyrimidines, aminopurines, aminopyrimidines, thiopurines, thiopyrimidines, indole, pyrrole, 7-deazaguanine, 7-methylguanine, hypoxanthine, pseudocytosines, pseudoisocytosines, isocytosines, isoguanine, 2-thiopyrimidines, 4-thiothymine, 6-thioguanine, nitropyrroles, nitroindoles, and 4-methylindole, without being limited thereto. Nucleotides including substituted deoxyribose analogs include substituted or unsubstituted arabinose, substituted or unsubstituted xylose, and substituted or unsubstituted pyranose. Nucleotides including phosphate eater analogs include alkylphosphonates, such as phosphorothioates, phosphorodithioates, phosphoramidates, phosphoroselenoates, phosphoranilothioates, phosphoraniladates, phosphoramidates, boron phosphates, phosphotriesters, and methylphosphonates.

In one embodiment, a reactant was adjusted to a total volume of 25 µl, and includes each F3 and B3 at a concentration of 0.2 µM, each FIP and BIP at a concentration of 1.6 µM, each LF and LB primer at a concentration of 0.8 µM, 0.4 M betaine, 10 mM MgSO$_4$, 1.4 mM dNTPs, 1× ThermoPol reaction buffer (New England Biolabs), 8 U Bst DNA polymerase (New England Biolabs), 0.625 U AMV reverse transcriptase (Invitrogen), and 10 µl of a sample requiring analysis of influenza infection.

Next, the reactant is reacted at a temperature suitable for the activities of a DNA polymerase and a reverse transcriptase. The reaction temperature may be determined in consideration of a target nucleotide sequence and enzymes used in the reaction. The reactant is allowed to react for a time sufficient to amplify the target nucleic acids. Those skilled in the art will be able to determine the reaction time in consideration of the reaction conditions, for example, within a time period of 15 to 60 minutes, but the reaction time may vary depending on the amount of the target nucleic acids contained in a sample. For example, the reaction time may be increased to increase sensitivity.

In one embodiment, a DNA polymerase and a reverse transcriptase are used together. Thus, a reverse transcription reaction and an amplification reaction may be performed in one reaction, thereby increasing convenience. In particular, when samples, such as nasal discharge and blood, are directly used without isolating nucleic acids, RNA and DNA of influenza viruses are all present in these samples, so that efficient amplification is possible. In the RT-LAMP reaction according to the present invention, since reverse transcribed DNA as well as DNA may be amplified, DNA and/or RNA of proviruses may be amplified.

The LAMP analysis according to the present invention may be performed in a variety of analysis formats, for example, in the form of a liquid phase reaction or with several components adsorbed to a solid substrate.

The primer according to the present invention, a composition or kit including the same, and a method using the same are used to analyze any biological sample that may be infected with influenza viruses by a LAMP technique. The amplified product has a sequence corresponding to the molecule used as a template, and may be analyzed by a variety of methods known in the art.

The amplified reaction product after amplification may be detected in various ways. For example, the color change and turbidity change of a reaction solution depending on DNA synthesis, fluorescence and/or electrophoresis may be used. The detected products are compared to the products of positive and/or negative control samples to quantitatively or qualitatively analyze influenza infection.

In one embodiment, the amplified products according to the present invention may be detected by the color change of a reaction solution depending on DNA synthesis. In this case, the reaction liquid may contain an appropriate indicator, and for example, hydroxy naphthol blue (HNB), a dye whose color changes depending on the concentration of magnesium ions in a reaction solution, may be used. The color of the product of the reaction is compared with that of the products of positive and/or negative control samples to quantitatively or qualitatively analyze influenza infection. Especially, since detection is possible with eyes, convenience may be increased.

In another embodiment, nucleic acids contained in an amplified product may be detected by a direct or indirect method. In the direct method, a detectably labeled primer may be used, and it is possible to confirm whether target nucleic acids are amplified by detecting a signal emitted from the labeled primer, which is specifically bound to the target nucleic acids. The detection may be performed in real time. In the indirect detection method, a labeled probe capable of binding to the amplified nucleic acids may be used. As used herein, a detectably labeled probe is a probe labeled with a substance capable of emitting a signal which may be detected by any suitable method, such as spectroscopic, optical, photochemical, biochemical, enzymatic, electrical, and/or immunochemical methods. Examples of the substances include fluorescence moieties, chemiluminescent moieties, bioluminescent moieties, magnetic particles, enzymes, substrates, radioactivity, and chromophore materials.

In one embodiment, labels for detection include compounds capable of generating or eliminating a detectable fluorescent, chemiluminescent, or bioluminescent signal, such as light emitting, light scattering, and light absorbing materials, without being limited thereto. For example, labels described in a reference (Garman A., Non-Radioactive Labeling, Academic Press 1997) may be referred to. Examples of fluorescent materials include fluorescein (e.g., U.S. Pat. No. 6,020,481), rhodamine (e.g., U.S. Pat. No. 6,191,278), benzophenoxazine (e.g., U.S. Pat. No. 6,140,500), energy transfer fluorescent dyes containing donors and receptors (e.g., U.S. Pat. No. 5,945,526) and cyanide (e.g., WO1997-45539), lissamin, phycoerythrin, Cy2, Cy3, Cy3.5, Cy5, Cy5.5, Cy7, FluorX (Amersham), Alexa 350, Alexa 430, AMCA, BODIPY 630/650, BODIPY 650/665, BODIPY-FL, BODIPY-R6G, BODIPY-TMR, BODIPY-TRX, Cascade Blue, 6-FAM, fluorescein isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, tetramethylrhodamine, and/or Texas Red, without being limited thereto. Also, any fluorescence moiety capable of generating other detectable signals is included. Fluorescent dyes include 6-carboxyfluorescein, 2',4',1,4-tetrachlorofluorescein, and 2',4',5',7',1,4-hexachlorofluorescein, without being limited thereto. In one embodiment, SYBR-Green, 6-carboxyfluorescein ("FAM"), TET, ROX, VIC, or JOE is used as a fluorescent marker. In one embodiment, a probe labeled with two fluorescent materials, a reporting fluorescent material and an erasing fluorescent material, is used. In this case, fluorescent materials emitting a spectrum of wavelengths that can be distinguished from each other are used. In addition, compounds capable of enhancing and stabilizing binding of nucleic acids or affecting binding of nucleic acids may be used as a marker, and examples of the compounds include intercalators including ethidium bromide and SYBR-Green, minor groove binders, and crosslinkable functional groups, without being limited thereto. Also, a reference (Blackburn et al., eds. "DNA and RNA Structure" in Nucleic Acids in Chemistry and Biology (1996)) may be referred to.

In addition, when confirming whether non-specific amplification by non-specific binding of primers occurs, a non-specific nucleic acid binder, such as ethidium bromide or PicoGreen, may be added to a control group not containing a template, and an amplification reaction is performed. After the reaction, the amount of amplified products nonspecifically synthesized may be determined.

In another embodiment, as described above, the present invention refers to a primer set or a composition or kit for detecting influenza including the primer set.

The composition according to the present invention may include a primer set consisting of four or six primers, which are suitable for the types of influenza to be detected and are suitable for components used in a LAMP or RT-LAMP reaction except for a template.

In the kit according to the present invention, a primer set consisting of four or six primers, which are suitable for components used in a LAMP or RT-LAMP reaction except for a template and are suitable for the types of influenza to be detected, may be provided separately or in one tube. The kit according to the present invention further includes a positive control, a negative control, and instructions for use. As a negative control, a sample not containing nucleic acids may be included, and as a positive control group, nucleic acids extracted from one or more detection targets may be included.

The primer, kit, and composition according to the present invention may be used to detect influenza at a nucleic acid level in biological samples. That is, the primer, kit, and composition may be used in an amplification reaction for detecting influenza infection. Results obtained from samples suspected of having influenza infection are compared with the results of a control group or a reference group to determine the presence of the nucleic acids of influenza viruses. At this time, based on the increase of the nucleic acids of influenza or the quantitative change of the nucleic acids of influenza, it is possible to determine whether influenza infection occurs. In addition, in the case of receiving treatment after influenza infection, the effect of the treatment may be predicted through the above process.

Also, in this respect, the present invention relates to a method of detecting influenza viruses in biological samples to provide information necessary for detection, diagnosis, or prognosis of influenza.

The method of detecting influenza according to the present invention is performed using the primer set, the composition or kit. In one embodiment, the method includes a step of providing samples taken from subjects requiring influenza virus detection; a step of providing the primer set according to the present invention and performing a LAMP reaction or a RT-LAMP using the samples and the primer set to amplify target nucleic acids; and a step of analyzing the results of the LAMP reaction or the RT-LAMP reaction and comparing the reaction results of the samples with the reaction results of control samples to determine whether the samples are infected with influenza. At this time, when there is a change in the amount of the amplified products of the sample as compared with the control sample, the sample is judged to be infected with influenza.

The method according to the present invention may determine influenza infection using qualitative or quantitative analysis. For example, when the amount of target nucleotides is increased in a sample as compared to a negative control, or when influenza is not detected in a negative control, but a positive reaction has occurred in a sample, or when a certain amount or more is detected in a sample, the sample may be judged to be infected with influenza. The judgment or judgment criterion may be easily determined in consideration of standards in the art.

Samples, reagents, amplification methods, and reaction conditions used in the method of the present invention may be referred to the above description.

Hereinafter, the present invention will be described in detail with reference to the following examples. However, the examples are illustrative only and are not intended to limit the scope of the present invention.

The present invention may be practiced within the skill of those skilled in the art using conventional techniques for cell biology, cell culture, molecular biology, gene transformation techniques, microbiology, DNA recombinant techniques, unless otherwise indicated. In addition, a more detailed description of common technique may be found in the following references: Molecular Biotechnology (Bernard et al., ASM press 2014); Molecular Cloning, A Laboratory Manual, 4th Ed. (Sambrook et al., Cold Spring Harbor Laboratory Press 2012); Short Protocols in Molecular Biology, 5th Ed. (Ausubel F. et al. eds., John Wiley & Sons 2002).

EXAMPLES

Example 1. Preparation of Viral RNA Samples

Influenza A subtypes H1N1, H3N2, and pdm H1N1 and influenza B were obtained from the Korea Centers for Disease Control and Prevention, and were cultured in pathogen-free eggs. After culture, viral RNA was extracted from the cultured influenza viruses using the QIAamp Viral RNA Mini Kit (Qiagen, Germany) according to the manufacturer's instructions.

Example 2. Analysis of Primer Specificity Against Influenza Viruses Using RT-LAMP Herein, as RT-LAMP primers, primers capable of detecting influenza A subtype H3, influenza A pdm H1N1, influenza B, and all subtypes of influenza A, respectively, were designed.

Information on the gene sequences and genome sequences of pdm H1N1, H3, and influenza type B was obtained from GenBank and Global Initiative on Sharing All Influenza Data (GISAID), and the corresponding strains used are as follows: pdm H1N1: influenza A virus (AJBoston/DOA21/2011 (H1N1)); influenza A virus (A/Beijing/01/2009 (H1N1), H3N2: influenza A virus (A/Chicago/YGA_04002/2012 (H3N2); influenza A virus (A/Korea/3773/2014 (H3N2), and influenza B: influenza B virus (B/Georgia/04/2013); influenza B virus (B/Massachusetts/04/2014). The HA, Matrix, and NA gene sequences in the genomes of the strains were aligned with each other. Matrix gene sequences were used to design primers for detecting all subtypes of influenza type A, matrix and HA gene sequences were used to design primers for detecting pdm H1N1, and HA gene sequences were used to design primers for detecting H3 or influenza B.

Specifically, RT-LAMP primers were designed using the ClustalX multiple sequence alignment program. The primers were designed to have various sequences and combinations from the sequences of hemagglutinin (HA) gene, matrix gene, and neuraminidase (NA) gene regions, and the possibility as a primer was verified with the BLAST program (blast.ncbi.nlm.nih.gov/Blast.cgi website). Each primer sequence is optimal in terms of specificity and sensitivity among tested primers with various sequences and combinations, and the primers are also designed to be optimized for LAMP reactions. Further, since the FIP and BIP primers according to the present invention do not include a linker, a LAMP reaction may be performed more effectively as well as the production cost is low. The primers were synthesized by an external company, and primer sequences are shown in Tables 1-1, 1-2, 1-3, and 1-4 below.

TABLE 1-1

| Influenza Virus subtype | Primer Name | | Sequence (5' -> 3') |
|---|---|---|---|
| Influenza A subtype H3 | FIP | SEQ ID NO 1 | TTGRAAGCCATCACACTGAGGGTCATCAGATCCTTGATGGAGA |
| | BIP | SEQ ID NO 2 | AAGCCYACAGCAACTGTTACCCATGAGGCAACTAGTGACCT |
| | F3 | SEQ ID NO 3 | AGGTGAAATATGCRACAGTC |
| | B3 | SEQ ID NO 4 | TGTTAAACTCCAGTGTGCC |
| | LF | SEQ ID NO 5 | AGAGCATCTATTAGTGTGCAGT |
| | LB | SEQ ID NO 6 | TGTGCCGATTATGCCTC |
| Influenza A subtype H3 | FIP | SEQ ID NO 7 | TGGGAATGCTTCCATTTGGAGTGCTCAATAATGAGATCAGATGC |
| | BIP | SEQ ID NO 8 | GATCACATACGGGGCCTGTCGTACATTTCKCATYCCTGTTG |
| | F3 | SEQ ID NO 9 | CAGGGAATCTAATTGCTCCTAG |
| | B3 | SEQ ID NO 10 | TGCCTCTAGTTTGTTTCTCTG |
| | LF | SEQ ID NO 11 | AMTTGCATTTGCCAATGGGT |
| | LB | SEQ ID NO 12 | AGCAAARCACTCTCGAAATTGG |
| Influenza A subtype H3 | FIP | SEQ ID NO 13 | GCTTCCATTTGGAGTGATGCATKCCGAAGTGGGAAAAGCTCAAT |
| | BIP | SEQ ID NO 14 | GTAAACAGGATCACATACGGGGCGCATYCCTGTTGCCAATT |
| | F3 | SEQ ID NO 15 | AATTGCTCCTCGGGGTTA |
| | B3 | SEQ ID NO 16 | CCGAATATGCCTCTAGTTTG |
| | LF | SEQ ID NO 17 | GCCAATGGGTGCATCTGAT |
| | LB | SEQ ID NO 18 | GTCCCAGATATGTTAAGCAAARCAC |

TABLE 1-2

| Influenza Virus subtype | Primer Name | | Sequence (5' -> 3') |
|---|---|---|---|
| Influenza A subtype pdm H1N1 2009 | FIP | SEQ ID NO 19 | TGGGGACCGATGCTGTGAATCAGGAAGTGGCTTTTGGCCTAGT |
| | BIP | SEQ ID NO 20 | ACCACCAACCCACTAATCAGGCCCAGCCATCTGCTCCATAG |
| | F3 | SEQ ID NO 21 | AGGATGGGAACAGTGACCA |
| | B3 | SEQ ID NO 22 | CAACCTCCATGGCTTCCG |
| | LF | SEQ ID NO 23 | TGCTCACAGGTGGCACA |
| | LB | SEQ ID NO 24 | ATGAAAACAGGATGGTGCTAGC |
| Influenza A subtype pdm H1N1 2009 | FIP | SEQ ID NO 25 | TGAGACCGATGCTGTGAATCAGGAAGCTGCTTTTGGTCTAGT |
| | BIP | SEQ ID NO 26 | ACCACCAATCCACTAATCAGGTCCAGCCAYCTGTTCCATAG |
| | F3 | SEQ ID NO 21 | AGGATGGGAACAGTGACCA |
| | B3 | SEQ ID NO 22 | CAACCTCCATGGCTTCCG |
| | LF | SEQ ID NO 27 | GTTCACAAGTGGCACACAC |
| | LB | SEQ ID NO 28 | ATGAAAACAGAATGGTGCTGGC |
| Influenza A subtype pdm H1N1 2009 | FIP | SEQ ID NO 29 | TCCACAATGTAGGACCATGARCTAACATTGCTGGCTGGATC |
| | BIP | SEQ ID NO 30 | CAATGGAACGTGTTACCCAGGACTTTCAAATGATGACACTGAGC |
| | F3 | SEQ ID NO 31 | CCCATTGCATTTGGGTAAATG |
| | B3 | SEQ ID NO 32 | CTGCCGTTACACCTTTGT |
| | LF | SEQ ID NO 33 | TGCTGTGGAGAGTGWTTCAC |
| | LB | SEQ ID NO 34 | GAGGAGCTAAGAGAGCAATTGA |

TABLE 1-3

| Influenza Virus subtype | Primer Name | | Sequence (5' -> 3') |
|---|---|---|---|
| All subtypes of influenza A | FIP | SEQ ID NO 35 | ACATCTTCAAGTCTCTGCGCGATCGTACGTTCTCTCTATCRTCCC |
| | BIP | SEQ ID NO 36 | GAGGCTCTCATGGARTGGCTAAAGACGGTGAGCGTRAAYACAA |
| | F3 | SEQ ID NO 37 | AGTCTTCTAACCGAGGTCGA |
| | B3 | SEQ ID NO 38 | TGCAGTCCTCGCTCACTG |
| | LF | SEQ ID NO 39 | GCTTTGAGGGGGCCT |
| | LB | SEQ ID NO 40 | AGACCAATCCTGTCACCTCTRAC |
| All subtypes of influenza A | FIP | SEQ ID NO 41 | AGTCAGAGGTGACAGRATTGGTAARAACAGATCTTGAGGC |
| | BIP | SEQ ID NO 42 | TTGTGTTCACGCTCACCGTCCATTYCCATTKAGGGCATT |
| | F3 | SEQ ID NO 43 | CGCAGAGACTKGAARRTG |
| | B3 | SEQ ID NO 44 | RTCCATGTTATTTGGRTC |
| | LF | SEQ ID NO 45 | TGTCTTTAGCCAYTCCATGAGA |
| | LB | SEQ ID NO 46 | GAGGACTGCAGCGTAGAC |
| All subtypes of influenza A | FIP | SEQ ID NO 47 | AGTCAGAGGTGACARRATTGGTRAAYACAGATCTTGAGGCTC |
| | BIP | SEQ ID NO 48 | TTGTKTTCACGCTCACCGTCCATTCCCATTDAGGGCATT |
| | F3 | SEQ ID NO 49 | GAGATCGCRCAGAGACTKG |
| | B3 | SEQ ID NO 50 | AGTTTAACTGCTYTRTCCAT |
| | LF | SEQ ID NO 51 | CTTGTCTTTAGCCAYTCCATGA |
| | LB | SEQ ID NO 46 | GAGGACTGCAGCGTAGAC |

TABLE 1-4

| Influenza Virus subtype | Primer Name | | Sequence (5' -> 3') |
|---|---|---|---|
| Influenza B | FIP | SEQ ID NO 52 | TCAGCTGCTCGAATTGGCTTTCGGATCCTCAATTCACTCT |
| | BIP | SEQ ID NO 53 | CTGCGGTGGGAGTCTTATCCGTGACCAGTCTAATTGTCTCC |
| | F3  | SEQ ID NO 54 | GCATATGACCAGAGAGTGGAAG |
| | B3  | SEQ ID NO 55 | GGAGCTGTTAGCTATTACTGTT |
| | LF  | SEQ ID NO 56 | TGTCCTTCATTAAGACGCTCG |
| | LB  | SEQ ID NO 57 | TGGTCAAGAGCAGGCATTATC |
| Influenza B | FIP | SEQ ID NO 58 | AGCCRCCAATCTGAGAAACRTTCTATGGAGACTCAAATCCTCA |
| | BIP | SEQ ID NO 59 | AGAAGACGGAGGRCTACCACAAYAATTGTTCCTGTTTTCCCAG |
| | F3  | SEQ ID NO 60 | GGGAAGACCAAATTACTGTTTG |
| | B3  | SEQ ID NO 61 | TATTACTTTGCTCCTGCCAC |
| | LF  | SEQ ID NO 62 | CTCCRTTAGCAGATGAGGTGAA |
| | LB  | SEQ ID NO 63 | GYGGCAGAATTGTYGTTGA |
| Influenza B | FIP | SEQ ID NO 64 | TCAGGGACAATACATTACGCATATCGATAAAGGAGGAAGTAAACACTCA |
| | BIP | SEQ ID NO 65 | TAAACGGAACATTCCTCAAACACCACTCTGGTCATAGGCATTC |
| | F3  | SEQ ID NO 66 | AGGGACATGAACAACAAAGA |
| | B3  | SEQ ID NO 67 | CAAGTTTAGCAACAAGCCT |
| | LF  | SEQ ID NO 68 | TCAAACGGAACTTCCCTTCTTC |
| | LB  | SEQ ID NO 69 | GGATACAAGTCCTTATCAACTCTGC |
| Influenza B | FIP | SEQ ID NO 70 | CCATTGGCMAGCTTCAARGGTGAGCCTTACTACACAGGRGAA |
| | BIP | SEQ ID NO 71 | AAGGAAAGGGGTTTCTTCGGAGCTGCAATCATTCCTTCCCA |
| | F3  | SEQ ID NO 72 | CGGTGGATTAAACAAAAGCA |
| | B3  | SEQ ID NO 73 | ATGTGTATCCGTGCCAAC |
| | LF  | SEQ ID NO 74 | TGGGCAATTTCCTATGGCYT |
| | LB  | SEQ ID NO 75 | ATTGCTGGTTTCYTAGAAGGAG |

In the tables, Y represents T or C (pyrimidines), R represents G or A (purines), K represents G or T (keto), M represents A or C (amino), and W represents A or T (weak).

Four primers except LF and LB or six primers were added to a reaction mixture, and a RT-LAMP reaction was performed after adjusting the total volume of the mixture to 25 µl. The composition and components used in the reaction are the same except for the number of primers, and the composition and components are as follows. In a reaction mixture having a total volume of 25 µl, each F3 and B3 at a concentration of 0.2 µM, each FIP and BIP at a concentration of 1.6 µM, each LF and LB primer at a concentration of 0.8 µM, 0.4 M betaine, 10 mM MgSO$_4$, 1.4 mM dNTPs, 1× ThermoPol reaction buffer (New England Biolabs), 8 U Bst DNA polymerase (New England Biolabs), 0.625 U AMV reverse transcriptase (Invitrogen), 120 µM HNB (Sigma), and 10 µl of a sample requiring analysis of influenza infection or 50 ng of isolated RNA were included. When four primers were used, a RT-LAMP reaction was performed at 58° C. for 60 minutes, and when six primers were used, a RT-LAMP reaction was performed at 58° C. for 35 minutes. The Bst DNA polymerase was inactivated at 80° C. or higher, so the reaction was terminated by heating at 80° C. for 5 minutes.

Control groups used for determining the specificity of the influenza A- and influenza B-specific primers according to the present invention were shown in the respective figures, and amplification results were analyzed by color analysis and electrophoresis. The results are shown in FIGS. 1 to 4. A primer set corresponding to SEQ ID NO: 7 to SEQ ID NO: 12 was used in FIG. 1, a primer set corresponding to SEQ ID NO: 21, SEQ ID NO: 22, and SEQ ID NO: 25 to SEQ ID NO: 28 was used in FIG. 2, a primer set corresponding to SEQ ID NO: 58 to SEQ ID NO: 63 was used in FIG. 3, and a primer set corresponding to SEQ ID NO: 35 to SEQ ID NO: 40 was used in FIG. 4.

The color analysis was performed by adding a hydroxy naphthol blue (HNB) dye to a reaction solution. HNB acts as an indicator of the concentration of Mg$^{2+}$ ions. When Mg$^{2+}$ ions are not present, a reaction solution exhibits a light blue color, and when Mg$^{2+}$ ions are present, a reaction solution exhibits a purple color. Therefore, before a reaction, a reaction solution exhibits purple, and as a DNA synthesis reaction proceeds, the color of the reaction solution changes from purple to blue as the concentration of Mg$^{2+}$ ions decreases. The color change is a positive signal indicating that nucleic acids have been amplified. Qualitative and quantitative analysis is possible by observation with the eye or by measuring the absorbance at a wavelength of about 650 nm. Using the method according to the present invention, it is possible to see and analyze the results quickly and conveniently. In addition, qualitative and quantitative analysis may be performed by measuring absorbance at a wavelength of 650 nm using a spectrophotometer.

As shown in FIG. 1, when the influenza A subtype H3-specific primers according to the present invention were used, H3N2 was specifically detected. The same specificity was also observed for experiments performed using four primers (experimental results not shown).

Figure 2:
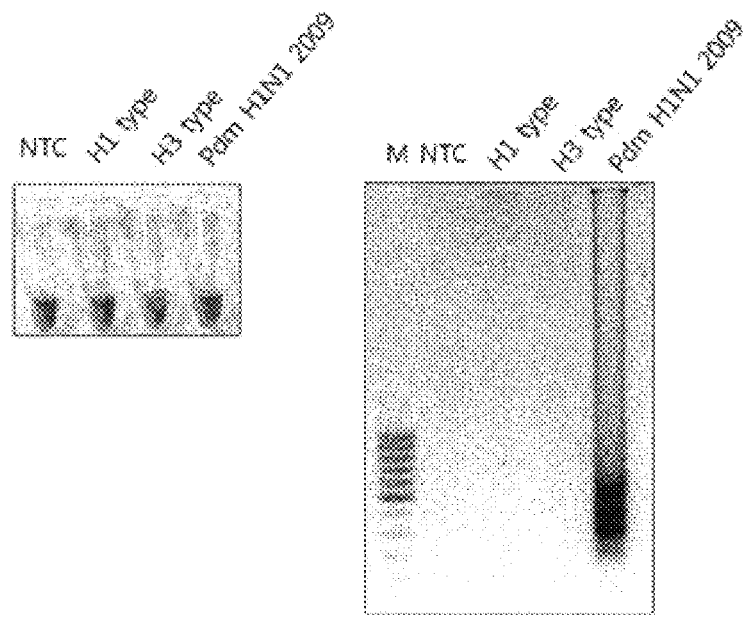
FIG. 2 shows the results of detecting the specificity of an influenza A subtype pdm H1N1-specific LAMP primer set having primers represented by SEQ ID NO: 21, SEQ ID NO: 22, and SEQ ID NO: 25 to SEQ ID NO: 28 via color changes and agarose gel electrophoresis.
Figure 3:
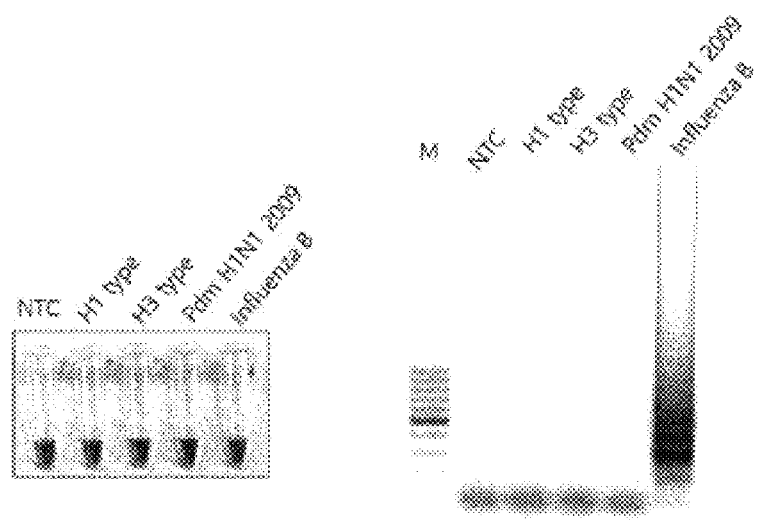
FIG. 3 shows the results of detecting the specificity of an influenza B-specific LAMP primer set including primers represented by SEQ ID NO: 58 to SEQ ID NO: 63 via color changes and agarose gel electrophoresis.

As shown in FIGS. 2 and 3, each of the influenza A pdm H1N1-specific primers and the influenza B-specific primers according to the present invention was able to specifically detect the corresponding influenza type. The same specificity was also observed for experiments performed using four primers (experimental results not shown).

Figure 4A:
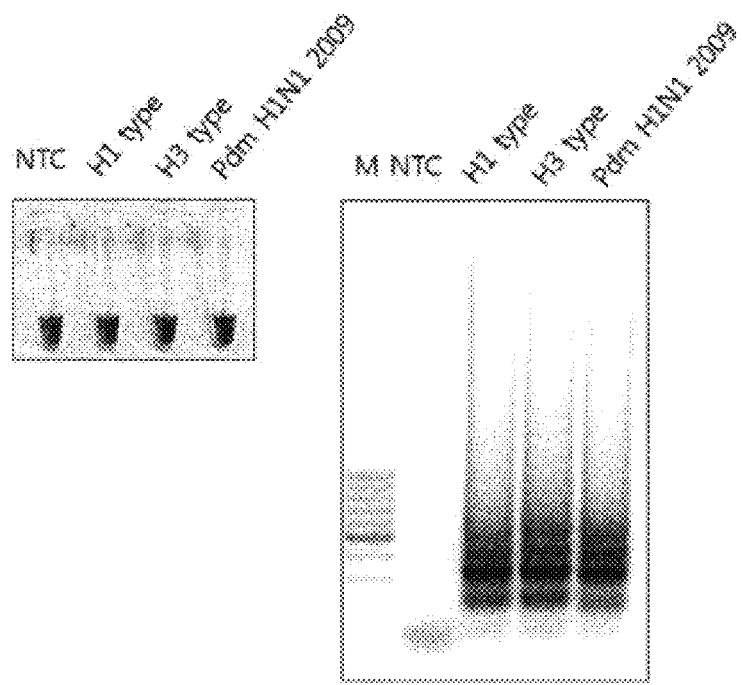
FIGS. 4A and 4B show the results of detecting the specificity of a LAMP primer set, capable of detecting all subtypes of influenza A, having primers represented by SEQ ID NO: 35 to SEQ ID NO: 40 via color changes and agarose gel electrophoresis.
Figure 4B:
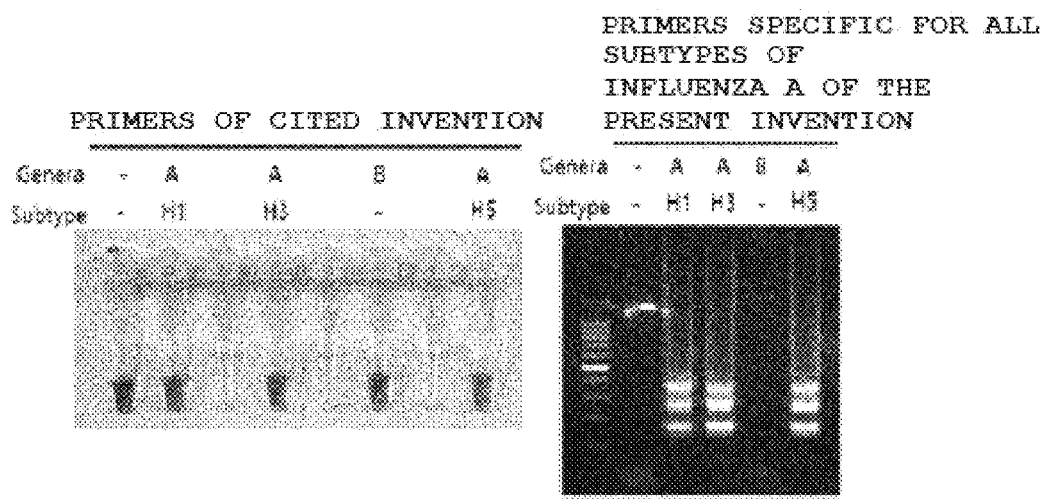
Figure 5:
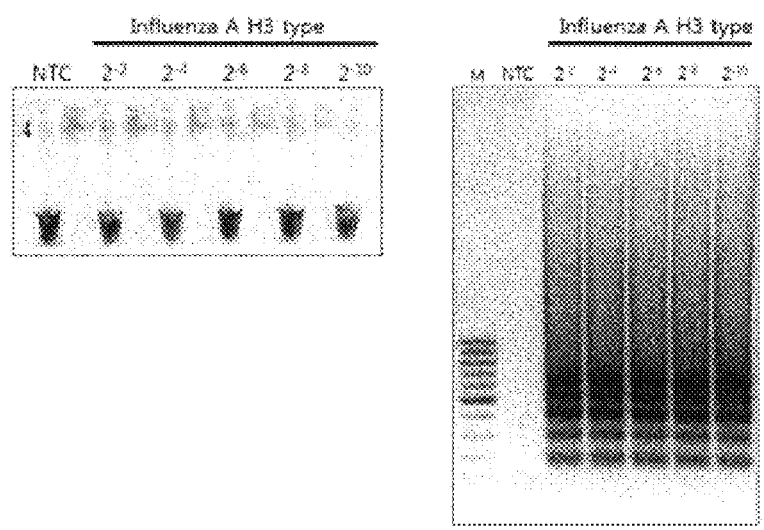
FIG. 5 shows the results of detecting the sensitivity of an influenza A subtype H3-specific LAMP primer set having primers represented by SEQ ID NO: 7 to SEQ ID NO: 12 via color changes and agarose gel electrophoresis.
Figure 6:
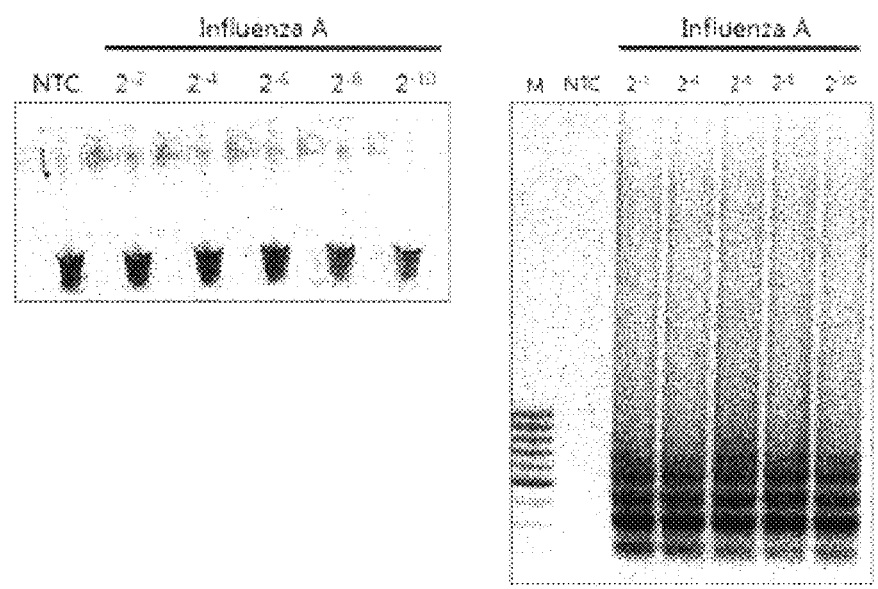
FIG. 6 shows the results of detecting the sensitivity of a LAMP primer set specific for all subtypes of influenza A having primers represented by SEQ ID NO: 35 to SEQ ID NO: 40 via color changes and agarose gel electrophoresis.

In addition, as shown in FIGS. 4a and 4b, all subtypes of influenza A used in this example were specifically, detected by the primers specific for all subtypes of influenza A, but influenza B was not detected by the primers. The same specificity was also observed for experiments performed using four primers (experimental results not shown). Therefore, the primers specific for all subtypes of influenza A may be usefully used to distinguish between influenza A and influenza B.

Example 3. Analysis of Primer Sensitivity Against Influenza Viruses Using RT-LAMP For analysis of primer sensitivity, the concentration of each viral RNA was varied to $2^{-2}$, $2^{-4}$, $2^{-6}$, $2^{-8}$, and $2^{-10}$ Tissue Culture Infective Dose 50 (TCID$_{50}$), and four or six primers were used as in Example 2 to perform LAMP reactions.

$2^{-2}$, $2^{-4}$, $2^{-6}$, $2^{-8}$, and $2^{-10}$ TCID$_{50}$ correspond to 2 ng, 0.2 ng, 20 pg, 2 pg, and 0.2 pg, respectively. Also, in the sensitivity analysis using each primer set in this example, when amplification is performed up to the minimum concentration, this does not indicate the limit of sensitivity detection.

Results are shown in FIGS. 5 to 16.

Figure 7:
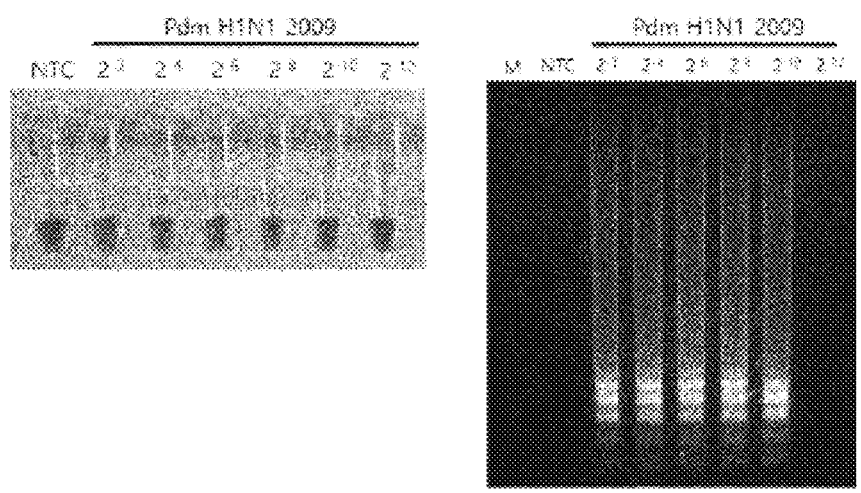
FIG. 7 shows the results of detecting the sensitivity of an influenza A subtype pdm H1N1-specific LAMP primer set having primers represented by SEQ ID NO: 21, SEQ ID NO: 22, and SEQ ID NO: 25 to SEQ ID NO: 28 via color changes and agarose gel electrophoresis.
Figure 8:
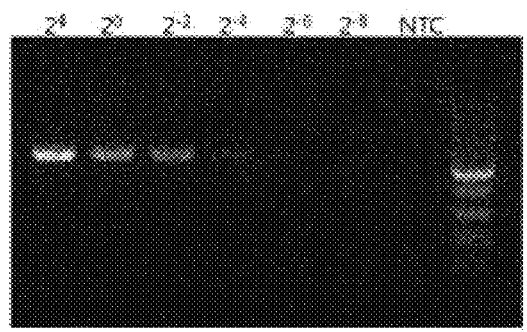
FIG. 8 shows the results of electrophoresis by manufacturing conventional primers for detecting influenza A subtype H3 and by performing RT-PCR.

Referring FIGS. 5 to 9, in the cases of influenza A H3-specific primers and primers specific for all subtypes of influenza A, since amplification also occurred at a minimum concentration of $2^{-10}$ PFU (FIGS. 5 and 6), the primers had a sensitivity corresponding to a concentration lower than the minimum concentration. The influenza A subtype pdm H1N1-specific primers exhibited a sensitivity of $2^{-10}$ PFU (FIG. 7). These results indicate that the LAMP reaction according to the present invention is superior to the conventional RT-PCR in terms of total time and sensitivity. In the case of a detection method of influenza A subtype H3 detection method (Infection Disease Laboratory Diagnosis-Disease-Specific Test, see cdc.go.kr/CDC/contents/CdcKrContentView.jsp?cid=18302&menuI ds=HOME001-MNU1175-MNU0834-MNU0839, Chapter 14 Influenza) of influenza detection methods presented by the Korea National Institute of Health, the method took 3 hours and was detectable up to $2^{-4}$ PFU (FIG. 8). On the other hand, when the primer set according to the present invention was used, the reaction time was shortened within 35 minutes, and detection was possible to less than $2^{-10}$ PFU. The same sensitivity was also observed for experiments performed using four primers (experimental results not shown).

In addition, the following primer sets were used to compare sensitivities: an influenza A subtype H3-specifi primer set including primers represented by SEQ ID NO: 1 to SEQ ID NO: 6, SEQ ID NO: 7 to SEQ ID NO: 12, or SEQ ID NO: 13 to SEQ ID NO: 18; an influenza A subtype pdm H1N1-specific primer set including primers represented by SEQ ID NO: 19 to SEQ ID NO: 24, SEQ ID NO: 21, SEQ ID NO: 22, and SEQ ID NO: 25 to SEQ ID NO: 28, or SEQ ID NO: 29 to SEQ ID NO: 34; a primer set specific for all subtypes of influenza A including primers represented by SEQ ID NO: 35 to SEQ ID NO: 40, SEQ ID NO: 41 to SEQ ID NO: 46, or SEQ ID NO: 46 and SEQ ID NO: 47 to SEQ ID NO: 51; and an influenza B-specific primer set including primers represented by SEQ ID NO: 52 to SEQ ID NO: 57, SEQ ID NO: 58 to SEQ ID NO: 63, SEQ ID NO: 64 to SEQ ID NO: 69, or SEQ ID NO: 70 to SEQ ID NO: 75. The sensitivities of two or three primer sets were compared and analyzed by influenza types. The concentration of each viral RNA was varied to 50 ng, 10 ng, 2 ng, 0.4 ng or 0.08 ng, and LAMP reactions were performed using four primers (except LF and LB in each primer set) or six primers in the same manner as in Example 2.

The results are described with reference to FIGS. 9 to 16.

Figure 9:
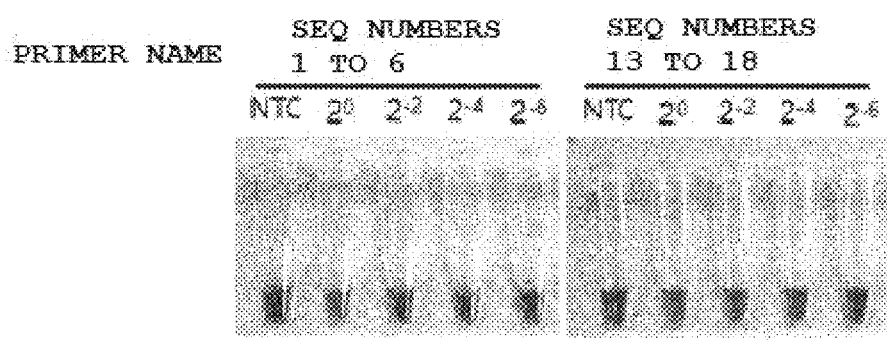
FIG. 9 includes images comparing the sensitivities of an influenza A subtype H3-specific LAMP primer set including primers represented by SEQ ID NO: 1 to SEQ ID NO: 6 and an influenza A subtype H3-specific LAMP primer set including primers represented by SEQ ID NO: 13 to SEQ ID NO: 18 by observing color change. The primer set corresponding to SEQ ID NO: 1 to SEQ ID NO: 6 exhibited a sensitivity of 2°, whereas, in the case of the primer set corresponding to SEQ ID NO: 13 to SEQ ID NO: 18, the sensitivity was less than $2^{-6}$ because amplification was performed up to a concentration threshold.
Figure 10:
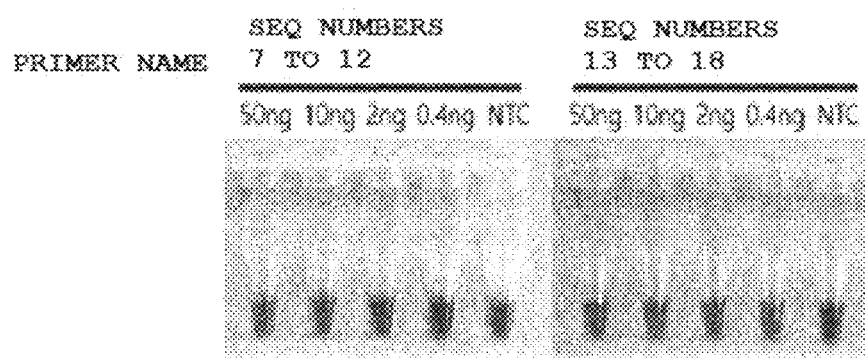
FIG. 10 includes images comparing the sensitivities of an influenza A subtype H3-specific LAMP primer set including primers represented by SEQ ID NO: 7 to SEQ ID NO: 12 and an influenza A subtype H3-specific LAMP primer set including primers represented by SEQ ID NO: 13 to SEQ ID NO: 18 by observing color change. The primer set corresponding to SEQ ID NO: 7 to SEQ ID NO: 12 exhibited a sensitivity of 2 ng, whereas, in the case of the primer set corresponding to SEQ ID NO: 13 to SEQ ID NO: 18, the sensitivity was less than 0.4 ng because color change was observed at a threshold of 0.4 ng. Based on the results of FIG. 17, the sensitivity was 2 pg.

In the case of the influenza A subtype H3-specific primers, as shown in FIG. 9, when the primer set corresponding to SEQ ID NO: 1 to SEQ ID NO: 6 was used, amplification also occurred at a minimum concentration of $2^{0}$, and when the primer set corresponding to SEQ ID NO: 13 to SEQ ID NO: 18 was used, amplification also occurred at a minimum concentration of $2^{-6}$. Thus, the respective primer sets exhibited a sensitivity corresponding to a lower concentration than the minimum concentration. In addition, as shown in FIG. 10, in the case of the primer set corresponding to SEQ ID NO: 7 to SEQ ID NO: 12, amplification also occurred at a minimum concentration of 2 ng, and in the case of the primer set corresponding to SEQ ID NO: 13 to SEQ ID NO: 18, amplification also occurred at a minimum concentration of 0.4 ng. Thus, the respective primer sets exhibited a sensitivity corresponding to a lower concentration than the minimum concentration.

Figure 11:
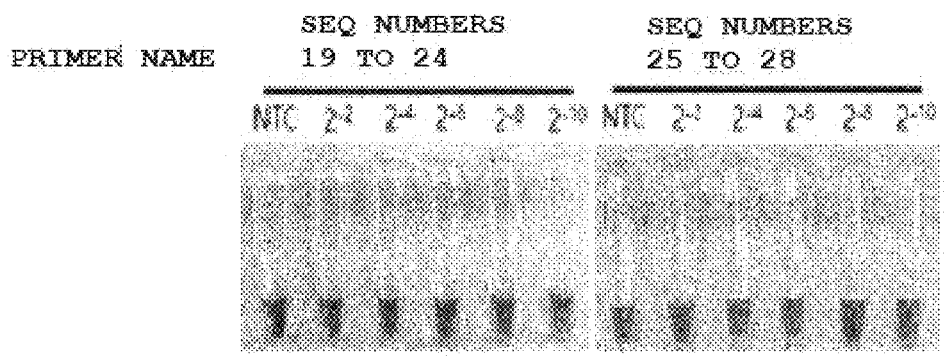
FIG. 11 includes images comparing the sensitivities of an influenza A subtype pdm H1N1-specific LAMP primer set including primers represented by SEQ ID NO: 19 to SEQ ID NO: 24 and an influenza A subtype pdm H1N1-specific LAMP primer set including primers represented by SEQ ID NO: 25 to SEQ ID NO: 28. Primers included in the primer set corresponding to SEQ ID NO: 19 to SEQ ID NO: 24 and primers included in the primer set corresponding to SEQ ID NO: 25 to SEQ ID NO: 28 were synthesized using matrix gene sequences. Each primer set includes primers corresponding to F3, B3, FIP, BIP, LF, and LB. In the two primer sets, primers used as F3 were the same, and primers used as B3 were the same. In addition, each of primers corresponding to FIP, BIP, LF, and LB was partially different in nucleotide sequence between the two primer sets. The primer set corresponding to SEQ ID NO: 19 to SEQ ID NO: 24 exhibited a sensitivity of $2^{-4}$, whereas the primer set corresponding to SEQ ID NO: 25 to SEQ ID NO: 28 (including SEQ ID NO: 21 and SEQ ID NO: 22) exhibited a sensitivity of $2^{-8}$.
Figure 12:
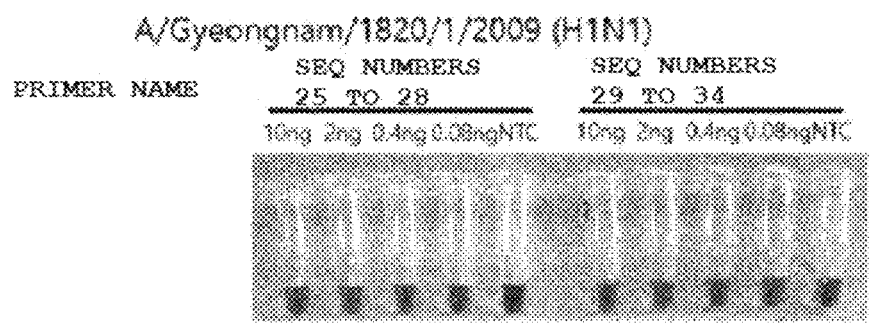
FIG. 12 includes images comparing the sensitivities of an influenza A subtype pdm H1N1-specific LAMP primer set including primers represented by SEQ ID NO: 25 to SEQ ID NO: (including SEQ ID NO: 21 and SEQ ID NO: 22) and an influenza A subtype pdm H1N1-specific LAMP primer set including primers represented by SEQ ID NO: 29 to SEQ ID NO: 34 by observing color change. The primers represented by SEQ ID NO: 21, SEQ ID NO: 22, and SEQ ID NO: 25 to SEQ ID NO: 28 were designed in a matrix gene region, and the primers represented by SEQ ID NO: 29 to SEQ ID NO: 34 were designed in a HA gene region. In the primer set corresponding to SEQ ID NO: 21, SEQ ID NO: 22, and SEQ ID NO: 25 to SEQ ID NO: 28 and the primer set corresponding to SEQ ID NO: 29 to SEQ ID NO: 34, color change was observed up to a threshold of 0.08 ng. These results indicate that the sensitivities of these primer sets are less than 0.08 ng. Based on the results of FIG. 18, the sensitivities are 2 pg.

In the case of the influenza A subtype pdm H1N1 primers, as shown in FIG. 11, the primer set corresponding to SEQ ID NO: 19 to SEQ ID NO: 24 exhibited a sensitivity of $2^{-4}$, and the primer set corresponding to SEQ ID NO: 25 to SEQ ID NO: (including SEQ ID NO: 21 and SEQ ID NO: 22) exhibited a sensitivity of $2^{-8}$. In addition, as shown in FIG. 12, the primer set corresponding to SEQ ID NO: 21, SEQ ID NO: 22, and SEQ ID NO: 25 to SEQ ID NO: 28 and the primer set corresponding to SEQ ID NO: 29 to SEQ ID NO: 34 were used, amplification also occurred at a minimum concentration of 0.08 ng. Thus, the respective primer sets exhibited a sensitivity corresponding to a lower concentration than the minimum concentration.

Figure 13:
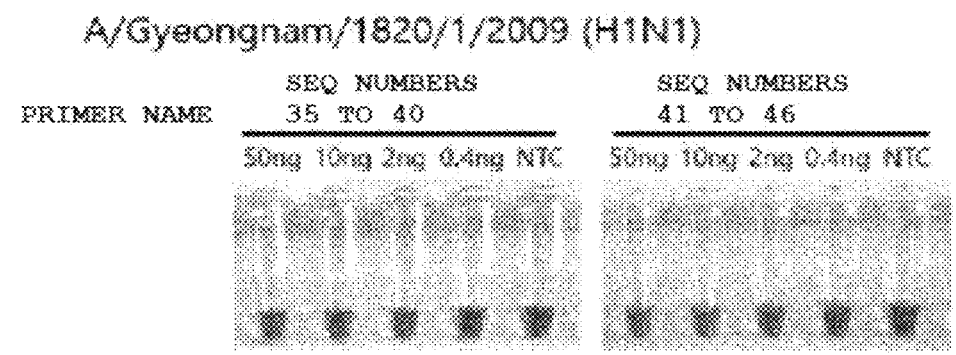
FIG. 13 includes images comparing the sensitivities of a LAMP primer set specific for all subtypes of influenza A including primers represented by SEQ ID NO: 35 to SEQ ID NO: and a LAMP primer set specific for all subtypes of influenza A including primers represented by SEQ ID NO: 41 to SEQ ID NO: 46 by observing color change. The primer set corresponding to SEQ ID NO: 35 to SEQ ID, NO: 40 exhibited a sensitivity of 2 ng. In the primer set corresponding to SEQ ID NO: 41 to SEQ ID NO: 46, color change was observed up to a threshold. This result indicates that the sensitivity of the primer set corresponding to SEQ ID NO: 41 to SEQ ID NO: 46 is less than 0.4 ng.
Figure 14:
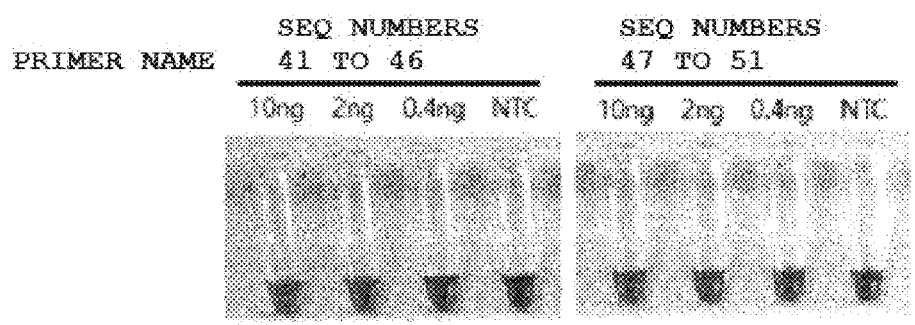
FIG. 14 includes images comparing the sensitivities of a LAMP primer set specific for all subtypes of influenza A including primers represented by SEQ ID NO: 41 to SEQ ID NO: 46 and a LAMP primer set specific for all subtypes of influenza A including primers represented by SEQ ID NO: 46 and SEQ ID NO: 47 to SEQ ID NO: 51 by observing color change. The primers represented by SEQ ID NO: 41 to SEQ ID NO: 46 and primers represented by SEQ ID NO: 46 and SEQ ID NO: 47 to SEQ ID NO: 51 were designed in a region similar to the matrix gene region, and these primers exhibited partial differences (within 5 bp per primer) in nucleotide sequences except for a LB primer. In the case of A/Brisbane/59/2007 (H1N1) samples, in the primer set corresponding to SEQ ID NO: 41 to SEQ ID NO: 46 and the primer set corresponding to SEQ ID NO: 46 and SEQ ID NO: 47 to SEQ ID NO: 51, color change was observed up to an experimental concentration threshold of 0.4 ng, thus indicating that the sensitivities of these primer sets are less than 0.4 ng. In the case of A/Korea/01/09 (H1N1 pdm) samples, in the primer set corresponding to SEQ ID NO: 41 to SEQ ID NO: 46, color change was observed up to an experimental concentration threshold of 0.4 ng, thus indicating that the sensitivity of the primer set is less than 0.4 ng. Also, in the primer set corresponding to SEQ ID NO: 46, SEQ ID NO: 47 to SEQ ID NO: 51, color change was observed up to an experimental concentration threshold of 0.4 ng, thus indicating that the sensitivity of the primer set is, less than 0.4 ng.
Figure 14:
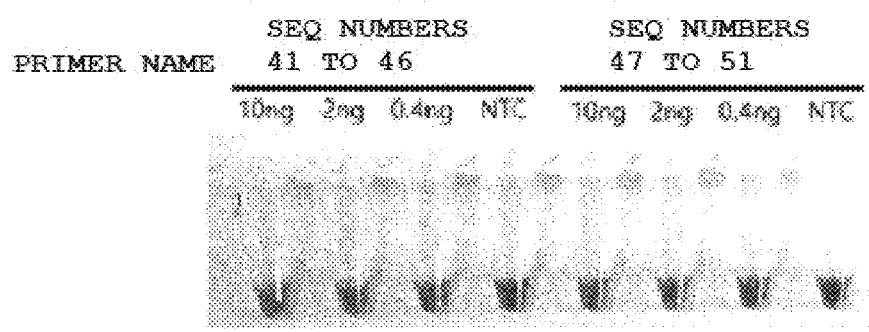

In the case of the primers specific for all subtypes of influenza A, as shown in FIG. 13, when the primer set corresponding to SEQ ID NO: 35 to SEQ ID NO: 40 was used, amplification also occurred at a minimum concentration of 2 ng, and when the primer set corresponding to SEQ ID NO: 41 to SEQ ID NO: 46 was used, amplification also occurred at a minimum concentration of 0.4 ng. Thus, the respective primer sets exhibited a sensitivity corresponding to a lower concentration than the minimum concentration. In addition, as shown in FIG. 14, in A/Brisbane/59/2007 (H1N1) samples, when the primer set corresponding to SEQ ID NO: 41 to SEQ ID NO: 46 and the primer set corresponding to SEQ ID NO: 46 and SEQ ID NO: 47 to SEQ ID NO: 51 were used, amplification also occurred at a minimum concentration of 0.4 ng. Thus, the respective primer sets exhibited a sensitivity corresponding to a lower concentration than the minimum concentration. In A/Korea/01/09 (H1N1 pdm) samples, when the primer set corresponding to SEQ ID NO: 41 to SEQ ID NO: 46 was used, amplification also occurred at a minimum concentration of 0.4 ng, and when the primer set corresponding to SEQ ID NO: 46 and SEQ ID NO: 47 to SEQ ID NO: 51 was used, amplification also occurred at a minimum concentration of 0.4 ng. Thus, the respective primer sets exhibited a sensitivity corresponding to a lower concentration than the minimum concentration.

Figure 15:
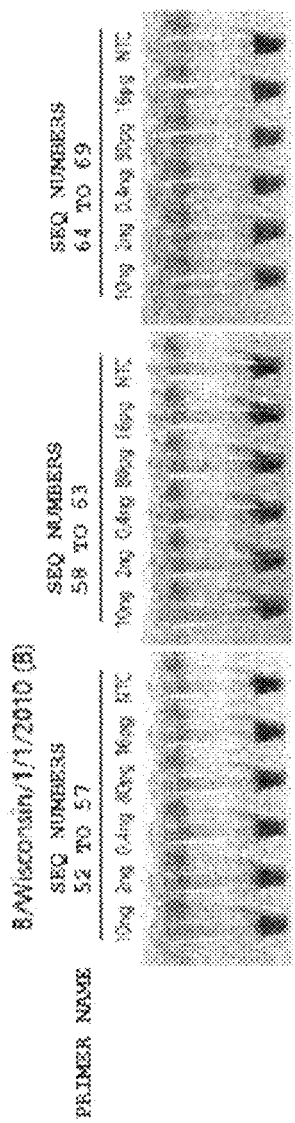
FIG. 15 includes images comparing the sensitivities of an influenza B-specific LAMP primer set including primers represented by SEQ ID NO: 52 to SEQ ID NO: 57, an influenza B-specific LAMP primer set including primers represented by SEQ ID NO: 58 to SEQ ID NO: 63, and an influenza B-specific LAMP primer set including primers represented by SEQ ID NO: 64 to SEQ ID NO: 69 by observing color change. The primers represented by SEQ ID NO: 52 to SEQ ID NO: 57 and the primers represented by SEQ ID NO: 64 to SEQ ID NO: 69 were designed in a NEP NS1 gene region, and the primers represented by SEQ ID NO: 58 to SEQ ID NO: 63 were designed in a HA gene region. The primer set corresponding to SEQ ID NO: 52 to SEQ ID NO: 57 and the primer set corresponding to SEQ ID NO: 58 to SEQ ID NO: 63 exhibited a sensitivity of 80 pg. In the primer set corresponding to SEQ ID NO: 64 to SEQ ID NO: 69, color change was observed up to an experimental concentration threshold of 16 pg, indicating that the sensitivity is less than 16 pg.
Figure 16:
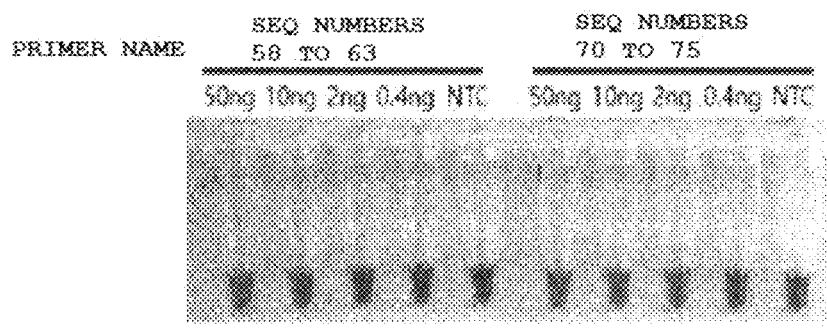
FIG. 16 includes images comparing the sensitivities of an influenza B-specific LAMP primer set including primers represented by SEQ ID NO: 58 to SEQ ID NO: 63 and an influenza B-specific LAMP primer set including primers represented by SEQ ID NO: 70 to SEQ ID NO: 75 by observing color change. In addition to the primer set corresponding to SEQ ID NO: 58 to SEQ ID NO: 63, other primer set corresponding to SEQ ID NO: 70 to SEQ ID NO: 75 was additionally designed in a HA gene region. The primers represented by SEQ ID NO: 58 to SEQ ID NO: 63 exhibited a sensitivity of 2 ng. In the primer set corresponding to SEQ ID NO: 70 to SEQ ID NO: 75, color change was observed up to an experimental concentration threshold of 0.4 ng, indicating that the sensitivity is less than 0.4 ng. Based on the results of FIG. 19, the sensitivity is 2 pg.

In addition, in the case of the influenza B-specific primers, as shown in FIG. 15, the primer set corresponding to SEQ ID NO: 52 to SEQ ID NO: 57 and the primer set corresponding to SEQ ID NO: 58 to SEQ ID NO: 63 exhibited a sensitivity of 80 pg, and when the primer set corresponding to SEQ ID NO: 64 to SEQ ID NO: 69 was used, amplification also occurred at a minimum concentration of 16 pg. Thus, the respective primer sets exhibited a sensitivity corresponding to a lower concentration than the minimum concentration. In addition, as shown in FIG. 16, the primer set corresponding to SEQ ID NO: 58 to SEQ ID NO: 63 exhibited a sensitivity of 2 ng, and when the primer set corresponding to SEQ ID NO: 70 to SEQ ID NO: 75 was used, amplification also occurred at a minimum concentration of 0.4 ng. Thus, the respective primer sets exhibited a sensitivity corresponding to a lower concentration than the minimum concentration.

In addition, as described above, in the sensitivity test for each primer, the sensitivity may not be judged to be the limit value when amplification is performed at the minimum concentration. Therefore, the same experiments as above were carried out using a lower concentration of influenza viruses.

Figure 17:
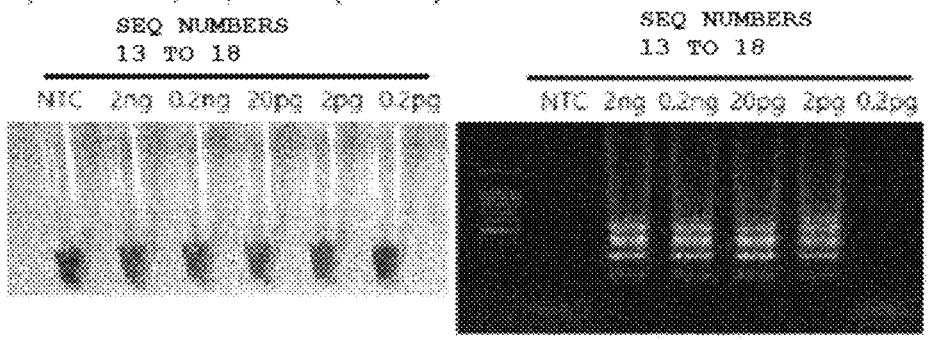
FIG. 17 shows the results of measuring the sensitivity of an influenza A subtype H3-specific LAMP primer set including primers represented by SEQ ID NO: 13 to SEQ ID NO: 18 by observing color change and using electrophoresis. In the analysis of FIG. 10, color change was observed up to a concentration threshold, and thus experiments were performed with influenza viruses at concentrations lower than the concentration tested in FIG. 10. As a result, the sensitivity of the primer set corresponding to SEQ ID NO: 13 to SEQ ID NO: 18 was 2 pg.
Figure 17:
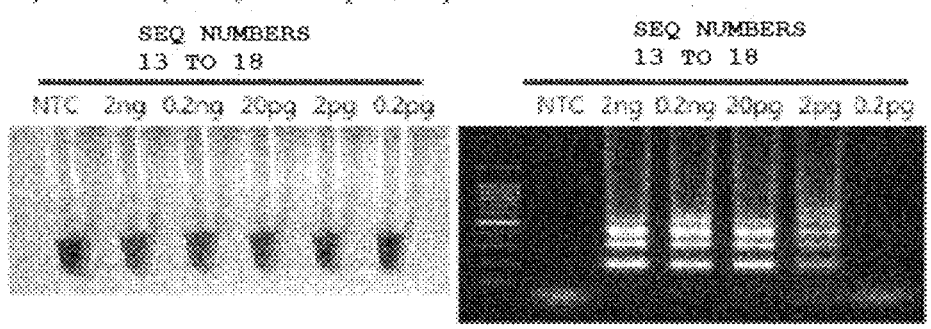
Figure 18:
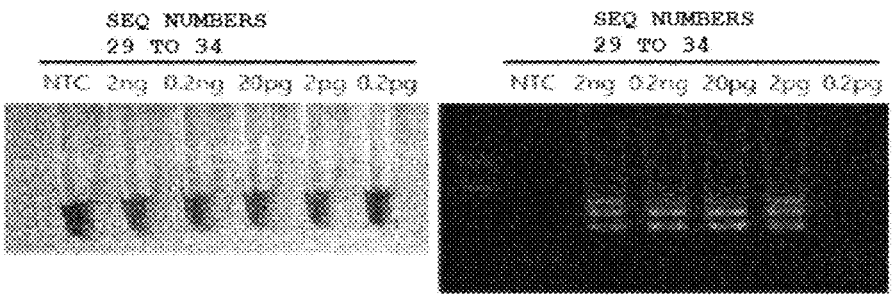
FIG. 18 shows the results of measuring the sensitivity of an influenza A subtype pdm H1N1-specific LAMP primer set including primers represented by SEQ ID NO: 29 to SEQ ID NO: 34 by observing color change and using electrophoresis. In the analysis of FIG. 12, color change was observed up to a concentration threshold, and thus experiments were performed with influenza viruses at concentrations lower than the concentration tested in FIG. 12. As a result, the sensitivity of the primer set corresponding to SEQ ID NO: 29 to SEQ ID NO: 34 was 2 pg.
Figure 18:
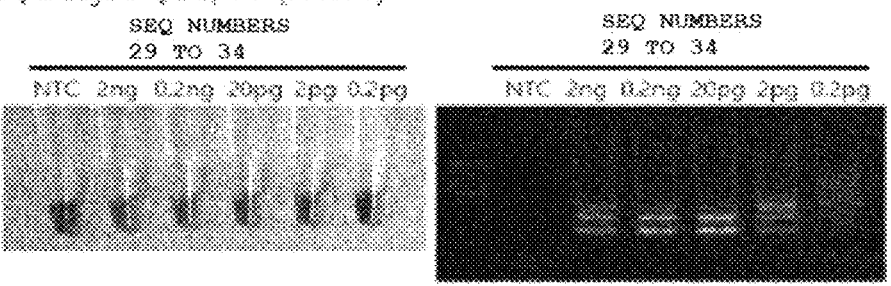

The results are shown in FIGS. 17 and 18.

FIG. 17 shows the results of measuring the sensitivity of an influenza A subtype H3-specific LAMP primer set including primers represented by SEQ ID NO: 13 to SEQ ID NO: 18 by observing color change and using electrophoresis. In the analysis of FIG. 10, color change was observed up to a concentration threshold, and thus experiments were performed with influenza viruses at concentrations lower than the concentration tested in FIG. 10. As a result, the sensitivity of the primer set corresponding to SEQ ID NO: 13 to SEQ ID NO: 18 was 2 pg.

FIG. 18 shows the results of measuring the sensitivity of an influenza A subtype pdm H1N1-specific LAMP primer set including primers represented by SEQ ID NO: 29 to SEQ ID NO: 34 by observing color change and using electrophoresis. In the analysis of FIG. 12, color change was observed up to a concentration threshold, and thus experiments were performed with influenza viruses at concentrations lower than the concentration tested in FIG. 12. As a result, the sensitivity of the primer set corresponding to SEQ ID NO: 29 to SEQ ID NO: 34 was 2 pg.

Figure 19:
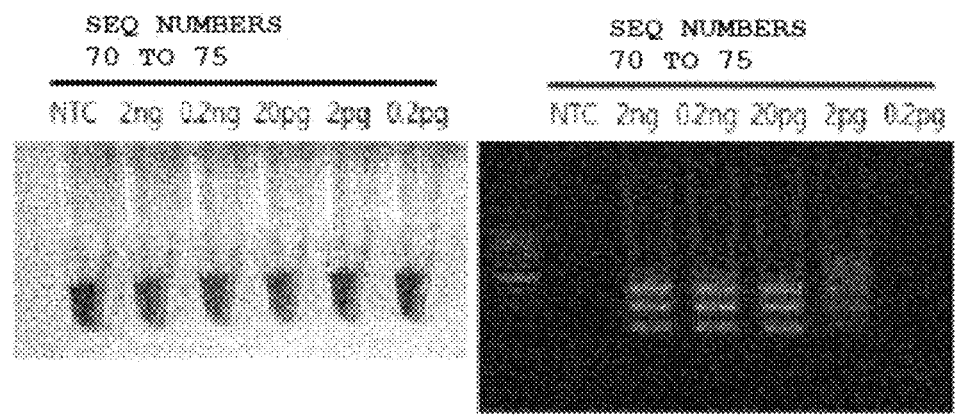
FIG. 19 shows the results of measuring the sensitivity of an influenza B-specific LAMP primer set including primers represented by SEQ ID NO: 70 to SEQ ID NO: 75 by observing color change and using electrophoresis. In the analysis of FIG. 16, color change was observed up to a concentration threshold, and thus experiments were performed with influenza viruses at concentrations lower than the concentration tested in FIG. 16. As a result, the sensitivity of the primer set corresponding to SEQ ID NO: 70 to SEQ ID NO: 75 was 2 pg.

FIG. 19 shows the results of measuring the sensitivity of an influenza B-specific LAMP primer set including primers represented by SEQ ID NO: 70 to SEQ ID NO: 75 by observing color change and using electrophoresis. In the analysis of FIG. 16, color change was observed up to a concentration threshold, and thus experiments were performed with influenza viruses at concentrations lower than the concentration tested in FIG. 16. As a result, the sensitivity of the primer set corresponding to SEQ ID NO: 70 to SEQ ID NO: 75 was 2 pg.

Unlike conventional methods which require agarose electrophoresis or separate equipment, the detection of amplification products according to the invention may also be achieved by visual observation of the color change of the reaction products after the amplification reaction. Therefore, convenience may be increased.

Although the exemplary examples of the present invention have been described in detail, it should be understood that the scope of the present invention is not limited thereto and that various modifications and improvements may be made by those skilled in the art using basic concepts defined in claims below, and thus the modifications and improvements also fall within the scope of the present invention.

Unless otherwise defined, all technical terms used in the present invention are used in a sense generally understood by those skilled in the art. The contents of all publications mentioned herein are incorporated herein by reference.

The invention claimed is:

1. A primer set for a LAMP analysis to detect influenza viruses, wherein the primer set is to detect influenza A or B, the primer set comprising at least one of:
   an influenza A subtype H3-specific primer set;
   an influenza A subtype pdm H1N1-specific primer set;
   an influenza A all subtype primer set; or
   an influenza B-specific primer set,
   wherein:
   the influenza A subtype H3-specific primer set is capable of distinguishing and detecting influenza A subtype H3, the influenza A subtype pdm H1N1-specific primer set is capable of distinguishing and detecting influenza A subtype pdm H1N1, and the influenza A all subtype primer set is capable of distinguishing and detecting influenza A regardless of subtypes thereof,
   the influenza A subtype H3-specific primer set comprises primers having base sequences represented by SEQ ID NO: 13 to SEQ ID NO: 16,
   the influenza A subtype pdm H1N1-specific primer set comprises primers having base sequences represented by SEQ ID NO: 29 to SEQ ID NO: 32,
   the influenza A all subtype primer set comprises primers having base sequences represented by at least one of: SEQ ID NO: 35 to SEQ ID NO: 38; SEQ ID NO: 41 to SEQ ID NO: 44; or SEQ ID NO: 47 to SEQ ID NO: 50, and
   the influenza B-specific primer set comprises primers having base sequences represented by SEQ ID NO: 70 to SEQ ID NO: 73.

2. The primer set according to claim 1,
   wherein the influenza A subtype H3-specific primer set further comprises primers represented by SEQ ID NO: 17 and SEQ ID NO: 18;
   wherein the influenza A subtype pdm H1N1-specific primer set further comprises primers represented by SEQ ID NO: 33 and SEQ ID NO: 34;
   wherein the influenza A all subtype primer set further comprises primers represented by at least one of: SEQ ID NO: 39 and SEQ ID NO: 40; SEQ ID NO: 45 and SEQ ID NO: 46; or SEQ ID NO: 51 and SEQ ID NO: 46; or
   wherein the influenza B-specific primer set further comprises primers represented by SEQ ID NO: 74 and SEQ ID NO: 75.

3. A primer set for a LAMP analysis to detect influenza viruses, the primer set being selected from the group consisting of an influenza A subtype H3-specific primer set, an influenza A subtype pdm H1N1-specific primer set, an influenza A all subtype primer set an influenza B-specific primer set, and combinations thereof, wherein the primer set comprises:
   the influenza A subtype H3-specific primer set comprising primers having base sequences represented by at least one of: SEQ ID NO: 1 to SEQ ID NO: 4; SEQ ID NO: 7 to SEQ ID NO: 10; or SEQ ID NO: 13 to SEQ ID NO: 16;
   the influenza A subtype pdm H1N1-specific primer set comprising primers having base sequences represented by at least one of: SEQ ID NO: 19 to SEQ ID NO: 22; SEQ ID NO: 21, SEQ ID NO: 22, SEQ ID NO: 25, and SEQ ID NO: 26; or SEQ ID NO: 29 to SEQ ID NO: 32;
   the influenza A all subtype primer set comprising primers having base sequences represented by at least one of: SEQ ID NO: 35 to SEQ ID NO: 38; SEQ ID NO: 41 to SEQ ID NO: 44; or SEQ ID NO: 47 to SEQ ID NO: 50; and
   the influenza B-specific primer set comprising primers having base sequences represented by at least one of: SEQ ID NO: 52 to SEQ ID NO: 55; SEQ ID NO: 58 to SEQ ID NO: 61; SEQ ID NO: 64 to SEQ ID NO: 67; or SEQ ID NO: 70 to SEQ ID NO: 73.

4. The primer set according to claim 3,
   wherein the influenza A subtype H3-specific primer set further comprises primers represented by at least one of: SEQ ID NO: 5 and SEQ ID NO: 6; SEQ ID NO: 11 and SEQ ID NO: 12; or SEQ ID NO: 17 and SEQ ID NO: 18;
   wherein the influenza A subtype pdm H1N1-specific primer set further comprises primers represented by at least one of: SEQ ID NO: 23 and SEQ ID NO: 24; SEQ ID NO: 27 and SEQ ID NO: 28; or SEQ ID NO: 33 and SEQ ID NO: 34;
   wherein the influenza A all subtype primer set further comprises primers represented by at least one of: SEQ ID NO: 39 and SEQ ID NO: 40; SEQ ID NO: 45 and SEQ ID NO: 46; or SEQ ID NO: 51 and SEQ ID NO: 46; and
   wherein the influenza B-specific primer set further comprises primers represented by at least one of: SEQ ID NO: 56 and SEQ ID NO: 57; SEQ ID NO: 62 and SEQ ID NO: 63; SEQ ID NO: 68 and SEQ ID NO: 69; or SEQ ID NO: 74 and SEQ ID NO: 75.

5. The primer set according to claim 1,
   wherein the LAMP is RT-LAMP.

6. The primer set according to claim 1,
   wherein one or more primers of the respective primer sets are labeled with a detectable labeling substance.

7. A method of detecting influenza viruses in vitro using the primer set according to claim 1, the method comprising:
   a step of providing samples taken from subjects requiring influenza virus detection;
   a step of providing the primer set according to claim 1;
   a step of performing a LAMP reaction using the samples and the primer set; and
   a step of analyzing results of the LAMP reaction, comparing the results of the LAMP reaction with LAMP reaction results of control samples, and determining the samples are infected with influenza if there is a difference in the results.

8. The method according to claim 7,
   wherein the LAMP reaction is RT-LAMP.

9. The method according to claim 7,
wherein the samples are one or more of whole blood, plasma, serum, lymph, urine, saliva, tears, or nasopharyngeal secretions.

10. The method according to claim 7,
wherein the step of analyzing results of the LAMP reaction is performed by measuring one or more of color change or turbidity of the reactants.

11. A composition for detecting influenza viruses, comprising the primer set according to claim 1.

12. A kit for detecting influenza viruses, comprising the primer set according to claim 1.

13. The primer set of claim 1, wherein the primer set comprises:
the influenza A subtype H3-specific primer set;
the influenza A subtype pdm H1N1-specific primer set; and
the influenza A all subtype primer set.

14. The primer set of claim 1, wherein the primer set comprises:
the influenza A subtype H3-specific primer set;
the influenza A subtype pdm H1N1-specific primer set;
the influenza A all subtype primer set; and
the influenza B-specific primer set.

15. The primer set of claim 13,
wherein the influenza A subtype H3-specific primer set comprises primers represented by SEQ ID NO: 13 to SEQ ID NO: 18;
wherein the influenza A subtype pdm H1N1-specific primer set comprises primers represented by SEQ ID NO: 29 to SEQ ID NO: 34; and
wherein the influenza A all subtype primer set comprises primers represented by at least one of: SEQ ID NO: 35 to SEQ ID NO: 40; SEQ ID NO: 41 to SEQ ID NO: 46; or SEQ ID NO: 46 to SEQ ID NO: 51.

16. The primer set of claim 14,
wherein the influenza A subtype H3-specific primer set comprises primers represented by SEQ ID NO: 13 to SEQ ID NO: 18;
wherein the influenza A subtype pdm H1N1-specific primer set comprises primers represented by SEQ ID NO: 29 to SEQ ID NO: 34;
wherein the influenza A all subtype primer set comprises primers represented by at least one of: SEQ ID NO: 35 to SEQ ID NO: 40; SEQ ID NO: 41 to SEQ ID NO: 46; or SEQ ID NO: 46 to SEQ ID NO: 51; and
wherein the influenza B-specific primer set further comprises primers represented by SEQ ID NO: 70 to SEQ ID NO: 75.

17. The primer set of claim 3, wherein the primer set comprises:
the influenza A subtype H3-specific primer set;
the influenza A subtype pdm H1N1-specific primer set; and
the influenza A all subtype primer set.

18. The primer set of claim 3, wherein the primer set comprises:
the influenza A subtype H3-specific primer set;
the influenza A subtype pdm H1N1-specific primer set;
the influenza A all subtype primer set; and
the influenza B-specific primer set.

19. The primer set of claim 17,
wherein the influenza A subtype H3-specific primer set comprises primers represented by at least one of: SEQ ID NO: 1 to SEQ ID NO: 6; SEQ ID NO: 7 to SEQ ID NO: 12; or SEQ ID NO: 13 to SEQ ID NO: 18;
wherein the influenza A subtype pdm H1N1-specific primer set comprises primers represented by at least one of: SEQ ID NO: 19 to SEQ ID NO: 24; SEQ ID NO: 21, SEQ ID NO: 22, SEQ ID NO: 25, SEQ ID NO: 26, SEQ ID NO: 27 and SEQ ID NO: 28; or SEQ ID NO: 29 to SEQ ID NO: 34; and
wherein the influenza A all subtype primer set comprises primers represented by at least one of: SEQ ID NO: 35 to SEQ ID NO: 40; SEQ ID NO: 41 to SEQ ID NO: 46; or SEQ ID NO: 46 to SEQ ID NO: 51.

20. The primer set of claim 18,
wherein the influenza A subtype H3-specific primer set comprises primers represented by at least one of: SEQ ID NO: 1 to SEQ ID NO: 6; SEQ ID NO: 7 to SEQ ID NO: 12; or SEQ ID NO: 13 to SEQ ID NO: 18;
wherein the influenza A subtype pdm H1N1-specific primer set comprises primers represented by at least one of: SEQ ID NO: 19 to SEQ ID NO: 24; SEQ ID NO: 21, SEQ ID NO: 22, SEQ ID NO: 25, SEQ ID NO: 26, SEQ ID NO: 27 and SEQ ID NO: 28; or SEQ ID NO: 29 to SEQ ID NO: 34;
wherein the influenza A all subtype primer set comprises primers represented by at least one of: SEQ ID NO: 35 to SEQ ID NO: 40; SEQ ID NO: 41 to SEQ ID NO: 46; or SEQ ID NO: 46 to SEQ ID NO: 51; and
wherein the influenza B-specific primer set comprises primers represented by at least one of: SEQ ID NO: 52 to SEQ ID NO: 57; SEQ ID NO: 58 to SEQ ID NO: 63; SEQ ID NO: 64 to SEQ ID NO: 69; or SEQ ID NO: 70 to SEQ ID NO: 75.

* * * * *

SEQUENCE LISTING

```
<160> NUMBER OF SEQ ID NOS: 77

<210> SEQ ID NO 1
<211> LENGTH: 43
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 1
ttgraagcca tcacactgag ggtcatcaga tccttgatgg aga            43

<210> SEQ ID NO 2
<211> LENGTH: 41
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 2
aagccyacag caactgttac ccatgaggca actagtgacc t              41

<210> SEQ ID NO 3
<211> LENGTH: 20
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 3
aggtgaaata tgcracagtc                                      20

<210> SEQ ID NO 4
<211> LENGTH: 19
<212> TYPE: DNA
<213> ORGANISM: Artificial Sequence
<223> OTHER INFORMATION: "B3"
<220> FEATURE:
```

<223> OTHER INFORMATION: B3

<400> SEQUENCE: 4
tgttaaactc cagtgtgcc                                                    19

<210> SEQ ID NO 5
<211> LENGTH: 22
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 5
agagcatcta ttagtgtgca gt                                                22

<210> SEQ ID NO 6
<211> LENGTH: 18
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 6
tgtgccggat tatgcctc                                                     18

<210> SEQ ID NO 7
<211> LENGTH: 44
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 7
tgggaatgct tccatttgga gtgctcaata atgagatcag atgc                        44

<210> SEQ ID NO 8
<211> LENGTH: 41
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 8
gatcacatac ggggcctgtc gtacatttck catycctgtt g                           41

<210> SEQ ID NO 9
<211> LENGTH: 22
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 9
cagggaatct aattgctcct ag                                                22

<210> SEQ ID NO 10
<211> LENGTH: 21
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 10
tgcctctagt ttgtttctct g                                    21

<210> SEQ ID NO 11
<211> LENGTH: 20
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 11
amttgcattt gccaatgggt                                      20

<210> SEQ ID NO 12
<211> LENGTH: 21
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 12
agcaaarcac tctgaaattg g                                    21

<210> SEQ ID NO 13
<211> LENGTH: 44
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 13
gcttccattt ggagtgatgc atkccgaagt gggaaaagct caat            44

<210> SEQ ID NO 14
<211> LENGTH: 41
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 14
gtaaacagga tcacatacgg ggcgcatycc tgttgccaat t               41

<210> SEQ ID NO 15
<211> LENGTH: 18
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 15
aattgctcct cggggtta                                        18

<210> SEQ ID NO 16
<211> LENGTH: 20
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 16
ccgaatatgc ctctagtttg                                              20

<210> SEQ ID NO 17
<211> LENGTH: 19
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 17
gccaatgggt gcatctgat                                               19

<210> SEQ ID NO 18
<211> LENGTH: 25
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 18
gtcccagata tgttaagcaa arcac                                        25

<210> SEQ ID NO 19
<211> LENGTH: 42
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 19
tgggaccgat gctgtgaatc aggaagtggc ttttggccta gt                     42

<210> SEQ ID NO 20
<211> LENGTH: 41
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 20
accaccaacc cactaatcag gcccagccat ctgctccata g                      41

<210> SEQ ID NO 21
<211> LENGTH: 19
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 21
aggatgggaa cagtgacca                                               19

<210> SEQ ID NO 22
<211> LENGTH: 18
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 22
caacctccat ggcttccg                                                  18

<210> SEQ ID NO 23
<211> LENGTH: 17
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 23
tgctcacagg tggcaca                                                   17

<210> SEQ ID NO 24
<211> LENGTH: 22
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 24
atgaaaacag gatggtgcta gc                                             22

<210> SEQ ID NO 25
<211> LENGTH: 42
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 25
tgagaccgat gctgtgaatc aggaagctgc ttttggtcta gt                       42

<210> SEQ ID NO 26
<211> LENGTH: 41
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 26
accaccaatc cactaatcag gtccagccay ctgttccata g                        41

<210> SEQ ID NO 27
<211> LENGTH: 19
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 27
gttcacaagt ggcacacac                                                 19

<210> SEQ ID NO 28
<211> LENGTH: 22
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 28

```
atgaaaacag aatggtgctg gc                                          22

<210> SEQ ID NO 29
<211> LENGTH: 41
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 29
tccacaatgt aggaccatga rctaacattg ctggctggat c                     41

<210> SEQ ID NO 30
<211> LENGTH: 44
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 30
caatggaacg tgttacccag gactttcaaa tgatgacact gagc                  44

<210> SEQ ID NO 31
<211> LENGTH: 21
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 31
cccattgcat ttgggtaaat g                                           21

<210> SEQ ID NO 32
<211> LENGTH: 18
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 32
ctgccgttac acctttgt                                               18

<210> SEQ ID NO 33
<211> LENGTH: 20
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 33
tgctgtggag agtgwttcac                                             20

<210> SEQ ID NO 34
<211> LENGTH: 22
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 34
gaggagctaa gagagcaatt ga                                          22
```

<210> SEQ ID NO 35
<211> LENGTH: 45
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 35
acatcttcaa gtctctgcgc gatcgtacgt tctctctatc rtccc    45

<210> SEQ ID NO 36
<211> LENGTH: 43
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 36
gaggctctca tggartggct aaagacggtg agcgtraaya caa    43

<210> SEQ ID NO 37
<211> LENGTH: 20
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 37
agtcttctaa ccgaggtcga    20

<210> SEQ ID NO 38
<211> LENGTH: 18
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 38
tgcagtcctc gctcactg    18

<210> SEQ ID NO 39
<211> LENGTH: 17
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 39
gctttgaggg ggcctga    17

<210> SEQ ID NO 40
<211> LENGTH: 23
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 40
agaccaatcc tgtcacctct rac    23

```
<210> SEQ ID NO 41
<211> LENGTH: 42
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 41
agtcagaggt gacagrattg gtaaraacac agatcttgag gc          42

<210> SEQ ID NO 42
<211> LENGTH: 39
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 42
ttgtgttcac gctcaccgtc cattyccatt kagggcatt             39

<210> SEQ ID NO 43
<211> LENGTH: 18
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 43
cgcagagact kgaarrtg                                    18

<210> SEQ ID NO 44
<211> LENGTH: 18
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 44
rtccatgtta tttggrtc                                    18

<210> SEQ ID NO 45
<211> LENGTH: 22
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 45
tgtctttagc caytccatga ga                               22

<210> SEQ ID NO 46
<211> LENGTH: 18
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 46
gaggactgca gcgtagac                                    18
```

```
<210> SEQ ID NO 47
<211> LENGTH: 42
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 47
agtcagaggt gacarrattg gtraayacag atcttgaggc tc          42

<210> SEQ ID NO 48
<211> LENGTH: 39
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 48
ttgtkttcac gctcaccgtc cattcccatt dagggcatt             39

<210> SEQ ID NO 49
<211> LENGTH: 19
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 49
gagatcgcrc agagactkg                                    19

<210> SEQ ID NO 50
<211> LENGTH: 20
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 50
agtttaactg ctytrtccat                                   20

<210> SEQ ID NO 51
<211> LENGTH: 22
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 51
cttgtctttt gccaytccat ga                                22

<210> SEQ ID NO 52
<211> LENGTH: 40
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 52
tcagctgctc gaattggctt tcggatcctc aattcactct             40

<210> SEQ ID NO 53
```

-continued

```
<211> LENGTH: 41
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 53
ctgcggtggg agtcttatcc gtgaccagtc taattgtctc c                          41

<210> SEQ ID NO 54
<211> LENGTH: 20
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 54
gcatatgacc agagtggaag                                                  20

<210> SEQ ID NO 55
<211> LENGTH: 22
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 55
ggagctgtta gctattactg tt                                               22

<210> SEQ ID NO 56
<211> LENGTH: 21
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 56
tgtccttcat taagacgctc g                                                21

<210> SEQ ID NO 57
<211> LENGTH: 21
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 57
tggtcaagag caccgattat c                                                21

<210> SEQ ID NO 58
<211> LENGTH: 43
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 58
agccrccaat ctgagaaacr ttctatggag actcaaatcc yca                        43

<210> SEQ ID NO 59
<211> LENGTH: 43
```

```
<212> TYPE: DNA
<213> ORGANISM: Artificial Sequence
<223> OTHER INFORMATION: "BIP"
<220> FEATURE:
<223> OTHER INFORMATION: BIP

<400> SEQUENCE: 59
agaagacgga ggrctaccac aayaattgtt cctgttttcc cag        43

<210> SEQ ID NO 60
<211> LENGTH: 22
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 60
gggaagacca aattactgtt tg        22

<210> SEQ ID NO 61
<211> LENGTH: 20
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 61
tattactttg ctcctgccac        20

<210> SEQ ID NO 62
<211> LENGTH: 22
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 62
ctccrttagc agatgaggtg aa        22

<210> SEQ ID NO 63
<211> LENGTH: 19
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 63
gyggcagaat tgtygttga        19

<210> SEQ ID NO 64
<211> LENGTH: 49
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 64
tcagggacaa tacattacgc atatcgataa aggaggaagt aaacactca        49

<210> SEQ ID NO 65
<211> LENGTH: 43
<212> TYPE: DNA
```

<213> ORGANISM: Artificial Sequence
<223> OTHER INFORMATION: "BIP"
<220> FEATURE:
<223> OTHER INFORMATION: BIP

<400> SEQUENCE: 65
taaacggaac attcctcaaa caccactctg gtcataggca ttc          43

<210> SEQ ID NO 66
<211> LENGTH: 20
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 66
agggacatga acaacaaaga          20

<210> SEQ ID NO 67
<211> LENGTH: 19
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 67
caagtttagc aacaagcct          19

<210> SEQ ID NO 68
<211> LENGTH: 23
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 68
tcaaacggaa cttcccttct ttc          23

<210> SEQ ID NO 69
<211> LENGTH: 25
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 69
ggatacaagt ccttatcaac tctgc          25

<210> SEQ ID NO 70
<211> LENGTH: 42
<212> TYPE: DNA
<213> ORGANISM: Artificial Sequence
<223> OTHER INFORMATION: "FIP"
<220> FEATURE:
<223> OTHER INFORMATION: FIP

<400> SEQUENCE: 70
ccattggcma gcttcaargg tgagccttac tacacaggrg aa          42

<210> SEQ ID NO 71
<211> LENGTH: 41
<212> TYPE: DNA
<213> ORGANISM: Artificial Sequence

<223> OTHER INFORMATION: "BIP"
<220> FEATURE:
<223> OTHER INFORMATION: BIP

<400> SEQUENCE: 71
aaggaaaggg gtttcttcgg agctgcaatc attccttccc a     41

<210> SEQ ID NO 72
<211> LENGTH: 20
<212> TYPE: DNA
<213> ORGANISM: Artificial Sequence
<223> OTHER INFORMATION: "F3"
<220> FEATURE:
<223> OTHER INFORMATION: F3

<400> SEQUENCE: 72
cggtggatta aacaaaagca     20

<210> SEQ ID NO 73
<211> LENGTH: 18
<212> TYPE: DNA
<213> ORGANISM: Artificial Sequence
<223> OTHER INFORMATION: "B3"
<220> FEATURE:
<223> OTHER INFORMATION: B3

<400> SEQUENCE: 73
atgtgtatcc gtgccaac     18

<210> SEQ ID NO 74
<211> LENGTH: 20
<212> TYPE: DNA
<213> ORGANISM: Artificial Sequence
<223> OTHER INFORMATION: "LF"
<220> FEATURE:
<223> OTHER INFORMATION: LF

<400> SEQUENCE: 74
tgggcaattt cctatggcyt     20

<210> SEQ ID NO 75
<211> LENGTH: 22
<212> TYPE: DNA
<213> ORGANISM: Artificial Sequence
<223> OTHER INFORMATION: "LB"
<220> FEATURE:
<223> OTHER INFORMATION: LB

<400> SEQUENCE: 75
attgctggtt tcytagaagg ag     22

<210> SEQ ID NO 76
<211> LENGTH: 20
<212> TYPE: DNA
<213> ORGANISM: Artificial Sequence
<223> OTHER INFORMATION: "AH3 BF (Fig.8)"
<220> FEATURE:
<223> OTHER INFORMATION: AH3 BF (Fig.8)

<400> SEQUENCE: 76
agcaaagctt tcagcaactg     20

<210> SEQ ID NO 77
<211> LENGTH: 20
<212> TYPE: DNA
<213> ORGANISM: Artificial Sequence
<223> OTHER INFORMATION: "AH3 BR (Fig.8)"

```
<220> FEATURE:
<223> OTHER INFORMATION: AH3 BR (Fig.8)

<400> SEQUENCE: 77
gcttccattt ggagtgatgc                                           20
```